(12) United States Patent
Verkman et al.

(10) Patent No.: US 12,038,430 B2
(45) Date of Patent: Jul. 16, 2024

(54) METHODS FOR HIGH-CONTENT DRUG SCREENING

(71) Applicant: The Regents of the University of California, Oakland, CA (US)

(72) Inventors: Alan S. Verkman, San Francisco, CA (US); Byung-Ju Jin, San Francisco, CA (US); Sujin Lee, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 667 days.

(21) Appl. No.: 17/046,099

(22) PCT Filed: Apr. 25, 2019

(86) PCT No.: PCT/US2019/029186
§ 371 (c)(1),
(2) Date: Oct. 8, 2020

(87) PCT Pub. No.: WO2019/236209
PCT Pub. Date: Dec. 12, 2019

(65) Prior Publication Data
US 2021/0033596 A1    Feb. 4, 2021

Related U.S. Application Data

(60) Provisional application No. 62/663,724, filed on Apr. 27, 2018.

(51) Int. Cl.
*G01N 33/50* (2006.01)
*B01L 3/00* (2006.01)

(52) U.S. Cl.
CPC .... *G01N 33/5008* (2013.01); *B01L 3/502715* (2013.01); *B01L 2200/027* (2013.01); *B01L 2300/0819* (2013.01); *B01L 2300/0861* (2013.01); *G01N 2800/382* (2013.01)

(58) Field of Classification Search
None
See application file for complete search history.

(56) References Cited

U.S. PATENT DOCUMENTS

| | | | |
|---|---|---|---|
| 5,807,683 A | 9/1998 | Brenner | |
| 5,958,792 A | 9/1999 | Desai et al. | |
| 6,004,617 A | 12/1999 | Schultz et al. | |
| 6,066,448 A * | 5/2000 | Wohlstadter | G01N 21/76 435/7.1 |
| 6,077,954 A | 6/2000 | Cook et al. | |
| 2009/0186776 A1* | 7/2009 | Webb | C12Q 1/6837 506/12 |
| 2015/0283099 A1* | 10/2015 | Podolski | A61K 45/06 514/648 |

FOREIGN PATENT DOCUMENTS

WO    199400805    4/1994

OTHER PUBLICATIONS

Holleran et al. "Pharmacological Rescue of the Mutant Cystic Fibrosis Transmembrane Conductance Regulator (CFTR) Detected by Use of a Novel Fluorescence Platform" Molecular Medicine, vol. 18, pp. 685-696, Feb. 29, 2012. (Year: 2012).*
Leggett et al. "Multicellular Tumor Invasion and Plasticity in Biomimetic Materials" Biomaterial Sci.; 5(8): 1460-1479 Jul. 25, 2017 ( Year: 2017).*
Alvarez-Lorenzo et al. (2013) "Crosslinked ionic polysaccharides for stimuli-sensitive drug delivery" Adv. Drug Deliv. Rev. 65(9):1148-1171.
Bailey et al. (2004) "Microarrays of small molecules embedded in biodegradable polymers for use in mammalian cell-based screens" Proc. Natl. Acad. Sci. USA. 101(46): 16144-16149.
Baldwin et al. (1995) "Synthesis of a Small Molecule Combinatorial Library Encoded with Molecular Tags" J. Am. Chem. Soc. 117(20):5588-5589.
Bellomo et al. (2017) "High-content drug screening for rare diseases" J. Inherit. Metab. Dis. 2017, 40: 601-607.
Cheong et al. (2010) "High-content screening in microfluidic devices" Expert Opin. Drug Discov., 5: 715-720.
Cil et al. (2016) "CFTR activator increases intestinal fluid secretion and normalizes stool output in a mouse model of constipation" Cell. Mol. Gastroenterol. Hepatol., 2: 317-327.
Demming et al. (2011) "Characterization of long-term stability of hydrophilized PEG-grafted PDMS within different media for biotechnological and pharmaceutical applications" Phys. Status Solid., 288: 1301-1307.
Dewitt et al. (1993) "Diversomers: An approach to nonpeptide, nonoligomeric chemical diversity" Proc. Nat. Acad. Sci. USA 90:6909-13.
Ding et al. (2105) "Microfluidic-enabled print-to-screen platform for high-throughput screening of combinatorial chemotherapy" Anal. Chern., 87: 10166-10171.
Esteva-Font et al. (2015) "Urea transporter proteins as targets for small-molecule diuretics" Nature Reviews Nephrology, 11:113-123.
Fujita et al. (2016) "A simple method for producing multiple copies of controlled release small molecule microarrays for cell-based screening" Biofabrication, 9, 011001.
Hanrahan et al. (2017) "Corrector combination therapies for F508del-CFTR" Curr. Opin. Pharmacal.,34: 105-111.
Hellmich et al. (2005) "Poly(oxyethylene) based surface coatings for poly(dimethylsiloxane) microchannels" Langmuir, 21: 7551-7557.
Huang et al. (2005) "Coating of poly(dimethylsiloxane) with n-dodecyl-β-D maltoside to minimize nonspecific protein adsorption" Lab Chip, 5: 1005-1007.
Hunkapiller et al. (1984) "A microchemical facility for the analysis and synthesis of genes and proteins" Nature 310:105-11.
Jin et al. (2013) "Microfluidics platform for single-shot dose response analysis of chloride channel modulating compounds" Lab Chip, 13(9): 3862-3867.
Jin et al. (2015) "Droplet-based microfluidic platform for measurement of rapid erythrocyte water transport" Lab Chip, 15:3380-3390.

(Continued)

*Primary Examiner* — Nancy J Leith
*Assistant Examiner* — Jessica D Parisi
(74) *Attorney, Agent, or Firm* — Edward J. Baba; Bozicevic, Field & Francis LLP

(57) ABSTRACT

Provided herein are methods and systems for screening a candidate agent to determine whether the candidate agent modulates an activity of cultured cells. Compositions for screening a candidate agent are also provided herein.

50 Claims, 15 Drawing Sheets

(56) References Cited

OTHER PUBLICATIONS

Jin et al. (2017) "Microfluidic platform for rapid measurement of transepithelial water transport" Lab Chip, 17: 887-895.

Kwon et al. (2011) Drug-eluting microarrays for cell-based screening of chemical-induced apoptosis. Anal. Chern., 83(11): 4118-4125.

Lee et al. (2012) "Alginate: properties and biomedical applications" Prog Polym Sci., 37: 106-126.

Lee et al. (2014) "High-throughput screening (HTS) of anticancer drug efficacy on a micropillar/microwell chip platform" Anal. Chern., 86: 535-542.

Li et al. (2017) "Therapeutic approaches to CFTR dysfunction: From discovery to drug development" J. Cyst. Fibros., 17(2): s14-s21.

Lillehoj et al. (2010) "A self-pumping lab-on-a-chip for rapid detection of botulinum toxin" Lab Chip, 10: 2265-2270.

Lillehoj et al. (2010) "A long-term, stable hydrophilic poly(dimethylsiloxane) coating for capillary based pumping" Proceedings of the IEEE 23rd International Conference on Micro Electro Mechanical Systems (MEMS), 1063-1066.

Mayr et al. (2009) "Novel trends in high-throughput screening" Curr. Opin. Pharmacal., 9: 580-588.

Mazutis et al. (2015) "Microfluidic production of alginate hydrogel particles for antibody encapsulation and release" Macromol. Biosci., 15: 1641-1646.

Mijnders et al. (2017) "Correcting CFTR folding defects by small molecule correctors to cure cystic fibrosis" Curr. Opin. Pharmacal., 34: 83-90.

Nestler et al. (1994) "A General Method for Molecular Tagging of Encoded Combinatorial Chemistry Libraries" J. Org. Chem. 59(17): 4723-4724.

Ohlmeyer et al. (1993) "Complex synthetic chemical libraries indexed with molecular tags" Proc. Nat. Acad. Sci. USA 90(23): 10922-10926.

Papadopoulos et al. (2014) "Treatment of neuromyelitis optica: state-of-the-art and emerging therapies" Nature Reviews Neurology, 10(9): 493-506.

Pedemonte et al. (2010) "Influence of cell background on pharmacological rescue of mutant CFTR" Am. J. Physiol. Cell Physiol., 298: C866-874.

Sun et al. (1998) "CombiDOCK: Structure-based combinatorial docking and library design" J. Comput. Aided Mol. Des. 12:597-604.

Tanaka et al. (1984) "Diffusion characteristics of substrates inCa-Alginate gel beads" Biotechnol. Bioeng., 26: 53-58.

Thiajarajah et al. (2015) "Secretory diarrhea: mechanisms and emerging therapies" Nature Reviews Gastroenterology Hepatology, 12:446-457.

Van Meer et al. (2017) "Small molecule absorption by PDMS in the context of drug response bioassays" Biochem. Biophys. Res. Commun., 482: 323-328.

Verkman et al. (2009) "Chloride channels as drug targets" Nature Reviews Drug Discovery, 8:153-171.

Verkman et al. (2014) "Aquaporins: important but elusive drug targets" Nature Reviews Drug Discovery, 13:259-277.

Wang et al. (2012) Quantitative analysis of molecular absorption into PDMS microfluidic channels, Ann Biomed Eng., 40: 1862-1873.

Whitesides et al. (2001) "Soft lithography in biology and biochemistry" Annu. Rev. Biomed. Eng., 3: 335-373.

\* cited by examiner

METHODS FOR HIGH-CONTENT DRUG SCREENING

CROSS REFERENCE

This application claims the benefit of PCT/US2019/029186, filed Apr. 25, 2019, which claims the benefit of U.S. Provisional Patent Application No. 62/663,724, filed Apr. 27, 2018, the disclosures of which are herein incorporated by reference.

STATEMENT REGARDING FEDERALLY SPONSORED RESEARCH

This invention was made with government support under Grant No. DK072517 awarded by the National Institutes of Health. The government has certain rights in the invention.

INTRODUCTION

Miniaturized high-throughput screening is needed in the pharmaceutical industry to accelerate drug discovery and reduce costs, and to advance personalized medicine utilizing limited quantities of patient-derived cells to treat, for example, cystic fibrosis, in which loss-of-function mutations in the cystic fibrosis transmembrane conductance regulator (CFTR) chloride channel cause lung and gastrointestinal disease by impairment of epithelial fluid transport. Screens for modulators of mutant CFTRs utilizing transfected heterologous cells have produced compounds of limited efficacy, such as correctors of defective CFTR-ΔF508 cellular processing. For example, it is known in the art that compounds identified from screens performed on transfected cells may not translate to primary, differentiated cultures of human cystic fibrosis airway cells grown on porous supports under native, air-liquid interface conditions. There is a need to develop screening methods utilizing primary, near-native patient-derived cystic fibrosis cells, which are generally limited in amount.

Limited progress has been made in high-content microarray screening methods using microdispenser technology. The general approach known in the art uses fabrication of confined microwells in which compounds are printed in separate wells or on pillars. However, these methods are at an early stage, with major challenges including well density, alignment of micropillars with wells, and cell culture in microwells. In addition, microwell methods are not suitable for epithelial cells cultured on porous filters at an air-liquid interface. In an early proof of concept study, a method was reported for cell exposure to test drugs in which a glass plate containing printed compounds is contacted with a cell culture. Major challenges with this approach, however, include cross-talk of neighboring compounds and the mechanics of making reliable contact between the glass plate containing test compound and the cell culture. The present disclosure addresses the above issues and provides related advantages.

SUMMARY

Provided herein are methods and systems for screening a candidate agent to determine whether the candidate agent modulates an activity of cultured cells. Compositions for screening a candidate agent are also provided herein.

In exemplary embodiments, the disclosed methods of screening a candidate agent to determine whether the candidate agent modulates an activity of cultured cells include positioning a hydrogel including at least one candidate agent in a lumen of a hollow micropillar, wherein the hollow micropillar includes a first surface having an open end and a second surface having a closed end in contact with a first substrate, wherein the hollow micropillar is orthogonal to the first substrate; bringing the first surface of the hollow micropillar into communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells; adding a solution to the interaction gap such that the at least one candidate agent is released from the hydrogel onto the surface of cultured cells; and measuring a signal from the cultured cells, wherein the signal indicates whether the at least one candidate agent modulates the activity of the cultured cells.

In some embodiments, the positioning includes filling the lumen of the hollow micropillar such that a surface of the hydrogel in the lumen is coplanar with the first surface of the hollow micropillar. In other embodiments, the positioning includes filling a portion of the lumen of the hollow micropillar. In certain aspects, the positioning includes printing the hydrogel by microinjection in the lumen of the hollow micropillar. In certain aspects, the hydrogel includes alginate.

In some embodiments, the hollow micropillar includes an inner diameter and an outer diameter. In certain aspects, the hollow micropillars are cylindrical in shape. In other aspects, the hollow micropillars are rectangular in shape. In some embodiments, the hollow micropillar includes a coating layer.

In some embodiments, the cultured cells include any cultured cell type such as eukaryotic cells and/or prokaryotic cells. In some embodiments, the cultured cells include epithelial cells; red blood cells; white blood cells such as neutrophils, eosinophils, basophils, lymphocytes; platelets; nerve cells; neuroglial cells; muscle cells; cartilage cells; bone cells; skin cells; endothelial cells; and/or fat cells. In some embodiments, the cultured cells are epithelial cells. In such embodiments, the cultured cells include filter-grown epithelial cells. In such embodiments, the epithelial cells express the cystic fibrosis transmembrane conductance regulator chloride (CFTR) channel. In some other embodiments, the cultured cells are non-epithelial cells including, but not limited to, cancerous cells and noncancerous cells. In some embodiments, the first surface of the hollow micropillar is in a spaced apart and in facing relationship with an apical surface of the cultured cells.

As described herein, the term "spaced apart and in facing relationship" may refer to a set distance between a first surface and a second surface, wherein the first surface and the second surface are facing each other, and wherein the set distance creates an interaction gap. In some embodiments, the interaction gap has a width of about 5 μm to about 150 μm, inclusive, such as 5 μm to 15 μm, 10 μm to 30 μm, 20 μm to 60 μm, 40 μm to 120 μm, and 80 μm to 150 μm, inclusive. In some embodiments, the interaction gap has a width of 10 μm. In other embodiments, the interaction gap has a width of 5 μm.

In some embodiments, the first substrate is in contact with a plurality of hollow micropillars such as two or more hollow micropillars or three or more hollow micropillars. In some embodiments, the hydrogel including the at least one candidate agent is positioned in the lumen of each hollow micropillar of the plurality of hollow micropillars. In some embodiments, each hollow micropillar is positioned at a set distance apart such that crosstalk between each hollow micropillar is reduced. In certain aspects, the set distance is the same between each hollow micropillar.

In some embodiments, the disclosed systems of screening a candidate agent to determine whether the candidate agent modulates an activity of cultured cells include a hollow micropillar, wherein a hydrogel including at least one candidate agent is positioned in a lumen of the hollow micropillar, wherein the hollow micropillar includes a first surface having an open end and a second surface having a closed end in contact with a first substrate, wherein the hollow micropillar is orthogonal to the first substrate; a plurality of cultured cells, wherein the first surface of the hollow micropillar is in communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells; a solution, wherein the solution is added to the interaction gap such that the at least one candidate agent is released from the hydrogel onto the surface of cultured cells; a processor unit; a non-transitory computer-readable storage medium including instructions, which when executed by the processor unit, cause the processor unit to measure a signal from the cultured cells, wherein the signal indicates whether the at least one candidate agent modulates the activity of the cultured cells.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
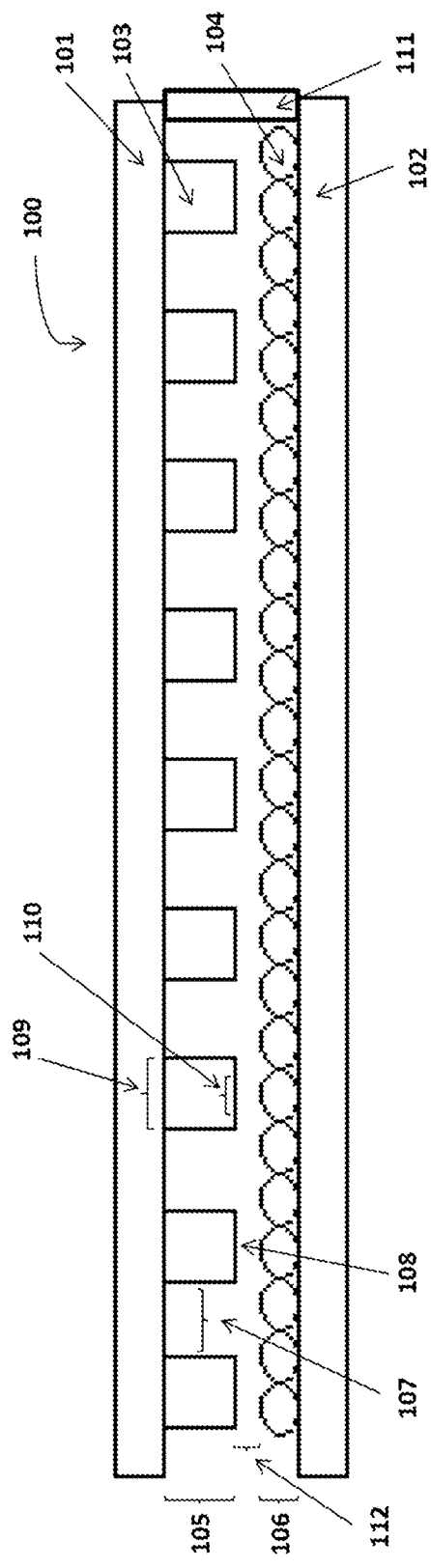
FIG. 1 depicts a schematic showing of a hollow micropillar array according to some embodiments disclosed herein.

As summarized above, provided herein are methods and systems for screening a candidate agent to determine whether the candidate agent modulates an activity of cultured cells. Compositions for screening a candidate agent are also provided herein.

The methods and systems disclosed herein provide an approach of screening a candidate agent to determine whether the candidate agent modulates an activity of cultured cells, including positioning a hydrogel including at least one candidate agent in a lumen of a hollow micropillar, wherein the hollow micropillar includes a first surface having an open end and a second surface having a closed end in contact with a first substrate, wherein the hollow micropillar is orthogonal to the first substrate; bringing the first surface of the hollow micropillar into communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells; adding a solution to the interaction gap such that the at least one candidate agent is released from the hydrogel onto the surface of cultured cells; and measuring a signal from the cultured cells, wherein the signal indicates whether the at least one candidate agent modulates the activity of the cultured cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a hydrogel" includes a plurality of such hydrogels and reference to "the hollow micropillar" includes reference to one or more hollow micropillars and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Compositions and Components

Figure 2A:
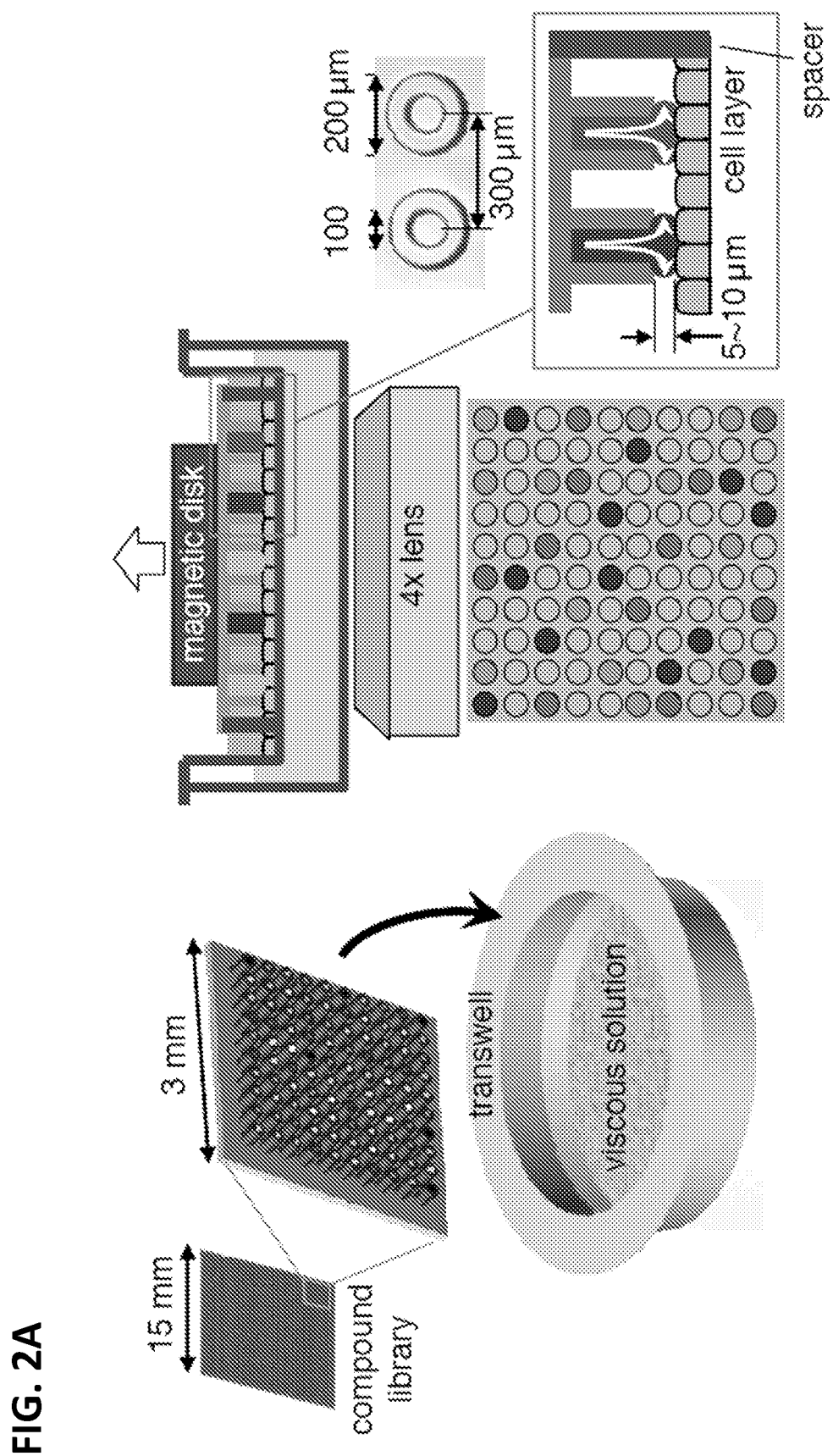
FIG. 2A-2B depict a hollow micropillar array as described herein to deliver compounds for high-content drug screening.

As summarized above, embodiments of the present disclosure include a composition for screening a candidate agent to determine whether the candidate agent modulates an activity of cultured cells. The composition may include, with reference to FIG. 1, a hollow micropillar array 100 including a hollow micropillar 103 disposed on a first substrate 101, having an outer diameter 109 and an inner diameter 110, a height 105, and a lumen 108 including a hydrogel; a candidate agent; and cultured cells 104 disposed on a second substrate 102, where the first substrate 101 and the second substrate 102 are in a spaced apart and in facing relationship, creating an interaction gap 112. In some embodiments, the present disclosure provides a practical high-content screening platform that may be applied to cells grown on a substrate or solid support including, but not limited to, plastic or nonporous filters. For example, as shown in FIG. 2A, compounds are printed in a hydrogel in a dense square array of hollow cylindrical micropillars that make close contact with the apical-facing surface of a cell culture including an epithelial cell monolayer.

In some embodiments, the present disclosure provides a high-content screening platform that may be applied to filter-grown primary epithelial cells, and, in general, to any cell culture system amenable to optical assay of gene function. In certain aspects, the present disclosure may include microtechnology such as microfabrication technology to fabricate hollow micropillar arrays, and microdispenser technology to print small volume of compounds in a hydrogel in the hollow micropillar array.

Hollow Micropillars

In some embodiments, the methods of screening a candidate agent to determine whether the candidate agent modulates an activity of cultured cells disclosed herein include positioning a hydrogel comprising at least one candidate agent in a lumen 108 of a hollow micropillar, wherein the hollow micropillar includes a first surface having an open end and a second surface having a closed end in contact with a first substrate 101, wherein the hollow micropillar is orthogonal to the first substrate 101.

As described herein, the terms "hollow micropillar" or "micropillar well" may be used interchangeably to refer to any three-dimensional raised surface of varying vertical dimension (height) and design upon which at least one candidate agent may be deposited in a lumen 108 of the hollow micropillar. A lumen 108 is a hollow conduit that extends through the shaft of the hollow micropillar such that the hollow micropillar includes a first surface having an open end, with an inner and outer diameter, and a second surface having a closed end in contact with a first substrate 101. Each hollow micropillar need not necessarily be in the form of a single, unitary pillar having a constant cross-sectional dimension along its height. Other designs with varying cross-sectional dimensions along the vertical dimension are included within the scope of the invention, so long as the other designs embody a substantially flat or planar first surface elevated out of the general plane of a substrate or support structure. In some embodiments, each hollow micropillar is orthogonal to the support structure.

In some embodiments, the geometry of a hollow micropillar may be optimized. For example, the height and inner and outer diameters of the hollow micropillar must be suitable for fabrication and printing, and permit sustained compound contact without cross-talk, the spacing between micropillars 107 determines the numbers of drug candidates that can be screened in a single measurement as well as compound exposure and/or cross-talk, and the hydrogel and overlying viscosities also determine compound exposure and/or cross-talk. Mathematical modeling of compound diffusion with different geometries and/or viscosities will guide parameter selection.

In some embodiments, a hollow micropillar has a height of about 50 µm to about 600 µm, inclusive, such as 50 µm to 150 µm, 100 µm to 300 µm, and 200 µm to 600 µm, inclusive. In certain embodiments, the hollow micropillar has a height of 150 µm. In some embodiments, a hollow micropillar has a cylindrical shape. In other embodiments, a hollow micropillar has a square shape, a rectangular shape, or a crescent shape.

In some embodiments, a hollow micropillar has an inner diameter 110 and an outer diameter 109. In certain embodiments, a hollow micropillar has an inner diameter 110 of about 50 µm to about 600 µm, inclusive, such as 50 µm to 150 µm, 100 µm to 300 µm, and 200 µm to 600 µm, inclusive. In certain embodiments, a hollow micropillar has an inner diameter 110 of 100 µm. In some embodiments, a hollow micropillar has an outer diameter 109 of about 60 µm to about 900 µm, inclusive, such as 60 µm to 150 µm, 120 µm to 300 µm, 200 µm to 600 µm, and 400 µm to 900 µm, inclusive. In certain embodiments, a hollow micropillar has an outer diameter 109 of 200 µm.

In some embodiments, a hollow micropillar includes a coating layer. In certain embodiments, the coating layer is hydrophilic and includes polydimethylsiloxane (PDMS) and/or polyethylene glycol (PEG). Further chemical modification of a surface of the hollow micropillar or any other portion thereof, may be employed to achieve desired bioreactive and bio-compatible properties. For example, a surface of a hollow micropillar may be modified with functional groups such as a coating of amino, carboxyl, hydroxyl, or anhydride groups, etc., which may permit candidate agents such as peptides, proteins, lipids, DNA, cell components, etc. to be immobilized by either covalent chemistry or non-covalent, electrostatic bonding. This coating layer may be either formed in situ on the hollow micropillar or later applied to the hollow micropillar.

In certain embodiments, the present disclosure provides an array of three-dimensional elevated surfaces such as hollow micropillar arrays that may be fabricated and experimentally studied by printing hydrogels with fluorescent dyes (in a subset of hollow micropillars) to study the diffusion by confocal microscopy. In some embodiments, each hollow micropillar functions as a microarray of candidate agents. Each hollow micropillar has physical dimensions that will allow at least one candidate agent to fit within its lumen 108. The present disclosure permits simultaneous, parallel analysis of a large variety of candidate agents under a multitude of experimental conditions while using a single assay device. Accordingly, each hollow micropillar may contain an experimental condition or reagent that is either the same or a different from another micropillar.

In some embodiments, each hollow micropillar is positioned at a set distance apart. In certain aspects, the set distance apart is the same between each hollow micropillar. In other aspects, the set distance apart is different between each hollow micropillar. In some embodiments, the set distance is about 100 μm to about 1000 μm, inclusive, such as 100 μm to 400 μm, 200 μm to 500 μm, 300 μm to 600 μm, 400 μm to 700 μm, 500 μm to 800 μm, 600 μm to 900 μm, and 700 μm to 1000 μm, inclusive. In some embodiments, the set distance is 300 μm.

In some embodiments, high-content screening using micropillar array technology may be demonstrated using small micropillar arrays and yellow fluorescent protein (YFP)/CFTR-expressing epithelial cell cultures. In some embodiments, a wide range of compounds may be dispensed, including chemically distinct CFTR activators. Solution handling and data acquisition and analysis methods may be optimized, and data quality (Z-factor, sensitivity, reproducibility) may be determined. In other embodiments, a large micropillar array (for example, a 50×50 micropillar array may test about 2500 compounds) may be fabricated and tested similarly as a small micropillar array. In some embodiments, an array of hollow micropillars may be of virtually any size or matrix configuration (e.g., 5×5, 10×10, 24×24, 30×30, 45×45, 50×50 etc.).

Hydrogels

As described herein, the term "hydrogel" may refer to a polymer cross-linked via covalent, ionic, or hydrogen bonds to provide a three-dimensional open-lattice structure that entraps water molecules to form a gel. Hydrogels can contain over 99% water and may include natural or synthetic polymers, or a combination thereof. In other instances, hydrogels may contain other percentages of water, as described herein. Hydrogels also possess a degree of flexibility due to their significant water content.

A hydrogel is needed to provide a mechanical framework for compound retention, as free-flowing aqueous solutions are easily disturbed during handling of the micropillar array. Hydrogels have found numerous applications in medical technology, for examples in implants or as drug delivery devices. A drawback with conventional hydrogels, such as polyHEMA (hydroxyethylmethacrylate), is their brittleness due to their low tensile strength in swollen state, which is about 0.5 MPa. To optimize the hydrogel for compound delivery, an alginate hydrogel may be used for compound stability and release after a few days of storage. In certain embodiments, the hydrogel may include alginate, agarose, and/or varying compositions of DMSO and salt concentrations, with endpoints including rates and percentage compound release at different times of storage. Compounds may include common drugs with a wide range of c log P values.

Alginate is a biodegradable polymer derived from seaweed. Alginate can be obtained from, for example, green algae (Chlorophyta), brown algae (Phaeophyta), and red algae (Rhodophyta). Alginate is a linear polysaccharide copolymer with two sterically different repeating units, (1→4)-α-L-guluronate (G unit) and (1→4)β-D-mannuronate (M unit) in varying proportions. Small molecule diffusion in alginate hydrogels is similar to their diffusion in the surrounding aqueous medium, as the alginate only includes a small volume fraction and small molecules are substantially smaller (<<1 nm) than the alginate pore size (5-16 nm). Various alternative hydrogels have been used for drug delivery such as poly(ethylene glycol) diacrylate (PEGDA) and poly-(D), (L)-lactide/glycolide copolymer (PLGA); however, compound release in these polymers occurs over hours or days, which is not suitable for methods described herein in which release over minutes is needed. Agarose and Matrigel® are not easily adapted for dispensing multiple compounds between of their rapid gelation and hence clogging of microneedles. The alginate hydrogel as described herein, with controlled calcium-dependent gelation, provides a stable vehicle to retain test compounds and release them into an overlying solution when needed.

Alginate useful in the disclosed hydrogels has a mannuronic acid to guluronic acid (MG) ratio of about 10% to about 90%, although other variations in composition may be used. In some embodiments, alginate useful in the disclosed hydrogels has a MG ratio of about 50% to about 70%. Alginate useful in the disclosed hydrogels has a molecular weight of from about 10 kDa to about 1000 kDa, although other molecular weights are contemplated. In some embodiments, alginate useful in the disclosed hydrogels has a molecular weight of from about 50 kDa to about 500 kDa. In some embodiments, alginate useful in the disclosed hydrogels has a molecular weight of from about 100 kDa to about 300 kDa. In some embodiments, alginate useful in the disclosed hydrogels has a molecular weight of about 240 kDa. Alginate useful in the disclosed hydrogels has a viscosity of from about 50 cP to about 600 cP (2% aqueous solution at 25° C.), inclusive such as 50 cP to 150 cP, 50 cP to 200 cP, 50 cP to 300 cP, 50 cP to 400 cP, and 50 cP to 500 cP, inclusive. In some embodiments, alginate useful in the disclosed hydrogels has a viscosity of from about 200 cP to 400 cP (2% aqueous solution at 25° C.).

In certain embodiments, an alginate hydrogel includes water in an amount of more than about 92% by weight of the hydrogel, e.g., about 92-99.9% by weight, or about 94%, 95%, 96%, 97%, 98%, 99% or 99.5% by weight, and a cross-linked alginate in an amount of about 0.1% to about 8% by weight of the hydrogel, e.g., about 6%, 5%, 4%, 3%, 2%, 1% or 0.5% by weight. In another embodiment, an alginate hydrogel includes a cross-linked alginate in an amount of about 2% by weight of the hydrogel. In another embodiment, an alginate hydrogel includes a cross-linked alginate in an amount of about 0.5% by weight of the hydrogel. In another embodiment, the alginate hydrogel includes additional additives. Various additives include, but are not limited to, one or more salts, amino acids, peptides, polypeptides, organic molecules, drugs, signaling molecules, antibiotics, vitamins, and the like.

Alginate hydrogels may be prepared by introducing an aqueous alginate solution into a solution of a water-soluble salt of a cation cross-linker. The cation salt solution can be stirred or can remain quiescent (e.g., not stirred). In an alternative arrangement, the stirred or quiescent cation salt solution can be added to the alginate solution. The alginate is introduced from a reservoir through a nozzle, syringe, or other applicator. The applicator diameter and fluid flow rates can be varied to vary the hydrogel thickness. Suitable modifications to this technique will be readily apparent to those of skill in the art.

In one or more embodiments, the alginate hydrogel has a diameter of about 50 μm to about 600 μm, inclusive, such as 50 µm to 150 µm, 100 µm to 300 µm, and 200 µm to 600 µm, inclusive. In certain embodiments, the alginate hydrogel has a diameter of 100 µm.

In some embodiments, the alginate in the alginate hydrogel may be cross-linked to enhance its structural integrity. In one or more embodiments, the alginate is cross-linked with a divalent or multivalent cation. Suitable cation cross-linkers include, but are not limited to, multivalent cations such as calcium, barium, strontium, copper, zinc, magnesium, manganese, cobalt, lead, iron, nickel, chromium, thorium, uranium, and aluminum, either alone or in combination with any of the above named cations. In one or more embodiments, the cation cross-linker is barium, either alone or in combination with any of the above named cations. The cation crosslinker can be calcium or barium or strontium or copper or zinc or magnesium or manganese or cobalt or lead or iron or nickel or chromium or thorium or uranium or aluminum.

Candidate Agents

In some embodiments, the present disclosure provides methods of screening a candidate agent to determine whether the candidate agent modulates an activity of cultured cells. The terms "candidate agent," "test agent," and "agent," are used interchangeably herein. Candidate agents encompass numerous chemical classes, typically synthetic, semi-synthetic, or naturally-occurring inorganic or organic molecules. Candidate agents include those found in large libraries of synthetic or natural compounds.

In certain aspects, the at least one candidate agent includes at least two candidate agents. In other aspects, the at least one candidate agent includes at least three candidate agents. In some other aspects, the at least one candidate agent includes at least four candidate agents or more. For example, in some embodiments, the at least one candidate agent includes at least one hundred candidate agents or more. In some embodiments, the at least one candidate agent includes at least one thousand candidate agents or more. In some embodiments, the at least one candidate agent includes at least ten thousand candidate agents or more.

The methods of the present disclosure include controls, where suitable controls include a sample in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Test agents may be small organic or inorganic compounds having a molecular weight of more than 50 and less than about 10,000 daltons, e.g., from about 50 daltons to about 100 daltons, from about 100 daltons to about 500 daltons, from about 500 daltons to about 1000 daltons, from about 1000 daltons to about 5000 daltons, or from about 5000 daltons to about 10,000 daltons. Test agents may include functional groups necessary for structural interaction with proteins, particularly hydrogen bonding, and may include at least an amine, carbonyl, hydroxyl or carboxyl group, and may contain at least two of the functional chemical groups. The test agents may include cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof. A test agent can be a peptide, a polypeptide, a natural product, or a synthetic peptide (e.g., where the synthetic peptide comprises one or more non-coded amino acid residues and/or a non-peptidic backbone).

Candidate agents of interest may include oligonucleotides, DNA, RNA, peptides, proteins, lipid membranes, or other nucleic or cellular matter that may be printed or otherwise immobilized in the lumen 108 of a hollow micropillar. Candidate agents of interest are biologically active agents that encompass numerous chemical classes, primarily organic molecules, which may include organometallic molecules, inorganic molecules, genetic sequences, etc. An important aspect of the invention is to evaluate candidate drugs for an effect on an activity of cultured cells. Candidate agents include functional groups necessary for structural interaction with proteins, particularly hydrogen bonding, and typically include at least an amine, carbonyl, hydroxyl or carboxyl group, frequently at least two of the functional chemical groups. The candidate agents often include cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Candidate agents may further include samples of unknown content. While many samples will include compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term "candidate agent" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

A variety of other reagents may be included in the methods described herein. These include reagents like salts, neutral proteins, e.g. albumin, detergents, etc., that are used to facilitate optimal binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, e.g., between 4 and 40° C. Incubation periods are selected for optimum activity, but may also be optimized to facilitate rapid high-throughput screening. Generally between 0.1 and 1 hour will be sufficient.

Agents that have an effect in a method of the present disclosure may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

Candidate agents are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Libraries of candidate compounds can also be prepared by rational design. (See generally, Cho et al., Pac. Symp. Biocompat. 305-16, 1998); Sun et al., J. Comput. Aided Mol. Des. 12:597-604, 1998); each incorporated herein by reference in their entirety). For example, libraries of phosphatase inhibitors can be prepared by syntheses of combinatorial chemical libraries (see generally DeWitt et al., Proc. Nat. Acad. Sci. USA 90:6909-13, 1993; International Patent Publication WO 94/08051; Baum, Chem. & Eng. News, 72:20-25, 1994; Burbaum et al., Proc. Nat. Acad. Sci. USA 92:6027-31, 1995; Baldwin et al., J. Am. Chem. Soc. 117: 5588-89, 1995; Nestler et al., J. Org. Chem. 59:4723-24, 1994; Borehardt et al., J. Am. Chem. Soc. 116:373-74, 1994; Ohlmeyer et al., Proc. Nat. Acad. Sci. USA 90:10922-26, all of which are incorporated by reference herein in their entirety.)

A "combinatorial library" is a collection of compounds in which the compounds including the collection are composed of one or more types of subunits. Methods of making combinatorial libraries are known in the art, and include the following: U.S. Pat. Nos. 5,958,792; 5,807,683; 6,004,617; 6,077,954, the disclosures of which are incorporated herein by reference. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing nonhydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Candidate agents of interest also include peptides and derivatives thereof, e.g. high affinity peptides or peptidomimetic substrates for the polypeptide of interest. Generally, peptide agents encompassed by the methods provided herein range in size from about 3 amino acids to about 100 amino acids, with peptides ranging from about 3 to about 25, inclusive, such as about 3 to about 12. Peptide agents can be synthesized by standard chemical methods known in the art (see, e.g., Hunkapiller et al., Nature 310:105-11, 1984; Stewart and Young, Solid Phase Peptide Synthesis, 2nd Ed., Pierce Chemical Co., Rockford, IL, (1984)), such as, for example, an automated peptide synthesizer. In addition, such peptides can be produced by translation from a vector having a nucleic acid sequence encoding the peptide using methods known in the art (see, e.g., Sambrook et al., Molecular Cloning, A Laboratory Manual, 3rd ed., Cold Spring Harbor Publish., Cold Spring Harbor, NY (2001); Ausubel et al., Current Protocols in Molecular Biology, 4th ed., John Wiley and Sons, New York (1999), disclosures of which are incorporated herein by reference).

Peptide libraries can be constructed from natural or synthetic amino acids. For example, a population of synthetic peptides representing all possible amino acid sequences of length N (where N is a positive integer), or a subset of all possible sequences, can comprise the peptide library. Such peptides can be synthesized by standard chemical methods known in the art (see, e.g., Hunkapiller et al., Nature 310:105-11, 1984; Stewart and Young, Solid Phase Peptide Synthesis, 2nd Ed., Pierce Chemical Co., Rockford, IL, (1984)), such as, for example, an automated peptide synthesizer. Nonclassical amino acids or chemical amino acid analogs can be used in substitution of or in addition into the classical amino acids. Non-classical amino acids include but are not limited to the D-isomers of the common amino acids, α-amino isobutyric acid, 4-aminobutyric acid, 2-amino butyric acid, γ-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

Substrates

The terms "substrate", "solid support", or "support structure" as used herein may include any rigid, substantially flat substrate or plate from which three-dimensional platforms project away. A substrate may, for example, form the base of a micro-titer plate or be the base of a monolayer culture. A substrate may be flat, fibrous, or 3-dimensional in nature. The substrate can also include a slide or pane of glass, ceramic, polymer, or plastic, or strips or sheets of metal. A "glass substrate," according to the invention, is any of various types of glass substrates such as untreated glass, antifog-treated glass, tempered glass, anti-reflection-treated glass, thermal ray blocking-treated glass, colored glass, and ITO conductive film-treated glass.

In one or more embodiments, a hollow micropillar includes a first surface having an open end and a second surface having a closed end in contact with a first substrate 101, wherein the hollow micropillar is orthogonal to the first substrate 101. In certain embodiments, the first substrate 101 is substantially planar and has a relatively large surface area for depositing an organized array of hollow micropillars. In some embodiments, the first substrate 101 includes polydimethylsiloxane.

In some aspects, the first substrate 101 and/or the second substrate 102 described herein may be either porous or nonporous and may be selected from either organic or inorganic materials. For example, the first substrate 101 and/or the second substrate 102 can include a plastic, a polymeric or co-polymeric substance, a ceramic, a glass, a metal, a crystalline material, a noble or semi-noble metal, a metallic or non-metallic oxide, an inorganic oxide, an inorganic nitride, a transition metal, or any combination thereof. Additionally, the first substrate 101 and/or the second substrate 102 may be configured so that it can be placed in any detection device. In one aspect, sensors may be integrated into the bottom/underside of the first substrate 101 and/or the second substrate 102, and used for subsequent detection. These sensors could include, but are not limited to, optical gratings, prisms, electrodes, and quartz crystal microbalances. Detection methods may include fluorescence, phosphorescence, chemiluminescence, refractive index, mass, and electrochemical. In one aspect, the first substrate 101 and/or the second substrate 102 is a resonant waveguide grating sensor.

In some aspects, the first substrate 101 and/or the second substrate 102 may include an inorganic material. Examples of inorganic support materials may include, but are not limited to, metals, glass or ceramic materials. Examples of metals that can be used as substrate materials may include, but are not limited to, gold, platinum, nickel, palladium, aluminum, chromium, steel, and gallium arsenide. Glass and ceramic materials used for the substrate material may include, but are not limited to, quartz, glass, porcelain, alkaline earth aluminosilicate glass and other mixed oxides. Further examples of inorganic substrate materials may include graphite, zinc selenide, mica, silica, lithium niobate, and inorganic single crystal materials.

In other aspects, the first substrate 101 and/or the second substrate 102 may include an organic material. Organic materials useful herein may be made from polymeric materials due to their dimensional stability and resistance to solvents. Examples of organic substrate materials may include, but are not limited to, polyesters, such as polyethylene terephthalate; polybutylene terephthalate; polypropylene; polyvinyl chloride; polyvinylidene fluoride; polytetrafluoroethylene; polycarbonate; polyamide; poly(meth) acrylate; polystyrene, polyethylene; cyclic polyolefins; ethylene/vinyl acetate or copolymers, or other known organic substrate materials.

In some aspects, the first substrate 101 and/or the second substrate 102 may be coated with one or more growth and/or differentiation substrates, such as collagen, fibronectin, laminin, vitronectin, D-lysine, and similar tissue culture substrates. The source of the growth and/or differentiation substrates may be from natural or synthetic sources. In certain aspects, the first substrate 101 and/or the second substrate 102 may be reactive.

In some embodiments, cultured cells adhere to the second substrate 102. Cultured cells may adhere to the second substrate 102 through non-covalent interactions such as, but not limited to ionic, hydrophobic or Van der Waals interactions. In such embodiments, the methods disclosed herein include bringing the first surface of the hollow micropillar into communication with a surface of cultured cells on a second substrate 102 to provide an interaction gap 112 between the first surface of the hollow micropillar and the surface of the cultured cells, wherein the first surface of the hollow micropillar is in a spaced apart and in facing relationship with the surface of cultured cells. In some embodiments, the second substrate 102 includes polydimethylsiloxane. In one or more embodiments, the first substrate 101 is held parallel to the second substrate 102 by e.g., a force. In certain embodiments, the second substrate 102 described herein provides a surface to support growth of the cultured cells thereon. The support provides, for example, a growth substrate for a cell monolayer across the surface of the substrate.

The methods described herein are generalizable to cell monolayers of any type grown on substrates, for example, solid or porous supports, and to kinetic or steady-state readout of an optical signal for any enzyme, transporter, receptor, or other target or a cell phenotype. In some embodiments, the methods use a limited quantity of cells, patient-derived primary cells for example, for screening and in assays utilizing limited quantities of test drugs. Further, assays of ion channels and solute transporters may be performed using suitable fluorescent indicators including, but not limited to, $Na^+$, $K^+$, $Cl^-$, pH, and membrane potential. Other possible read-outs include optical imaging cell shape and motility.

Cultured Cells

The methods disclosed herein may be generally applicable to cell monolayers of any type grown on solid or porous supports. Monolayer cultures refer to cells that have adhered to a substrate and grow in as a layer that is one cell in thickness 106. The surface on which cells are cultured is preferably a solid surface such as for example a glass or plastic culture plate, flask, dish, microtiter plate, chamber slide, coverslip or similar utensil. When grown on a solid surface cells may be cultured and maintained on feeder layers such as fibroblast feeder layers, or the surface may be coated with agents such as collagen or Matrigel®.

As used herein, the term "cancerous cell" may refer to a cell that is tumorigenic, i.e. it can initiate tumors in vivo. A cancerous cell may also be metastatic, i.e. it can initiate tumors at a secondary site in the primary host, or in secondary hosts.

Cells appropriate for use with the methods described herein may be any cells suitable for growth on a surface, such as eukaryotic cells, e.g., mammalian cells, such as human cells. The cultured cells may be normal cells such as noncancerous cells, or cancerous cells; virally-infected cells or non-infected cells; modified cells or non-modified cells; and cells expressing a particular gene, for example, a gene encoding a polypeptide, protein, cell surface receptor, growth factor, cytokine, antigen, and/or immunoglobulin. Exemplary cells include epithelial cells; red blood cells; white blood cells such as neutrophils, eosinophils, basophils, lymphocytes; platelets; nerve cells; neuroglial cells; muscle cells; cartilage cells; bone cells; skin cells; endothelial cells; and/or fat cells. The cells may be in a short-term primary cell culture or a long-term culture of an immortal cell line. In exemplary embodiments, any cultured cell type may be used. In some embodiments, the cells may be cells isolated from a human subject that may be immobilized on a coated support. In certain embodiments, the cultured cells include epithelial cells. In one or more embodiments, the cultured cells include filter-grown epithelial cells. In other embodiments, the cultured cells include non-epithelial cells.

In some other embodiments, the epithelial cells express the cystic fibrosis transmembrane conductance regulator chloride (CFTR) channel. Cystic fibrosis (CF) is a lethal autosomal recessive disorder in which abnormal regulation of epithelial Cl⁻ channels is associated with the pathophysiology of the disease. The CF gene has been cloned and sequenced and the amino acid sequence of the putative product (cystic fibrosis transmembrane conductance regulator, or CFTR) has been deduced. CFTR contains two membrane domains, each with six potential transmembrane segments, two nucleotide-binding folds (NBFs), and a highly charged cytoplasmic domain (R domain). The most common mutation associated with CF is the deletion of three nucleotides that would encode a phenylalanine at position 508 within the first NBF (exon 10). Both the NBFs and the R domain contain multiple potential phosphorylation sites for protein kinase A and protein kinase C. Protein kinases are important physiologic regulators of Cl— secretion, and defective regulation of outwardly rectifying Cl⁻ channels by protein kinases A and C is one defect in CF patients.

Other exemplary examples of cultured cells include, but are not limited to, polarized cells and/or non-polarized cells including epithelial cells; red blood cells; white blood cells such as neutrophils, eosinophils, basophils, and/or lymphocytes; platelets; nerve cells; neuroglial cells; muscle cells; cartilage cells; bone cells; skin cells; endothelial cells; and/or fat cells. In some embodiments, the cultured cells include patient-derived primary cells. In some other embodiments, the cultured cells include mammalian epithelial cells, such as Madin-Darby Canine Kidney (MDCK) cells, LLC PK1 porcine kidney cells, Caco-2 cells, CEBBe1 cells, HT-29 cells, T84 cells, and SK-CO15 cells, or derivative cells such as epithelial cells genetically engineered to express, or have reduced expression of CFTR, among others. In some embodiments, the polarized cells and non-polarized cells may be cultured on permeable tissue culture inserts and maintained in the presence of apical and basolateral tissue culture medium, especially in the form of a cell monolayer; however, these cell monolayers can also survive for extended periods of time in ambient conditions following the removal of the apical tissue culture medium.

Methods

As summarized above, the methods disclosed herein provide an approach of screening a candidate agent to determine whether the candidate agent modulates an activity of cultured cells, includes positioning a hydrogel including at least one candidate agent in a lumen 108 of a hollow micropillar, wherein the hollow micropillar includes a first surface having an open end and a second surface having a closed end in contact with a first substrate 101, wherein the hollow micropillar is orthogonal to the first substrate 101; bringing the first surface of the hollow micropillar into communication with a surface of cultured cells on a second substrate 102 to provide an interaction gap 112 between the first surface of the hollow micropillar and the surface of the cultured cells, wherein the first surface of the hollow micropillar is in a spaced apart and in facing relationship with the surface of cultured cells; adding a solution to the interaction gap 112 such that the at least one candidate agent is released from the hydrogel onto the surface of cultured cells; and measuring a signal from the cultured cells, wherein the signal indicates whether the at least one candidate agent modulates the activity of the cultured cells.

As described herein, the terms "modulating" or "modulate" may refer to the increasing or decreasing an activity of a cultured cell. The degree of modulation of an activity may depend on the at least one agent used, the activity to be modulated by the at least one candidate agent, and the particular assay used to measure that activity. One skilled in the art may determine a statistically significant change in the activity of the cultured cell that either constitutes an increase or decrease in the activity of the cultured cell that is being measured or that identifies the at least one candidate agent as agent(s) that increases or decreases the activity of the cultured cell that is being measured.

As described herein, the term "activity" of the cultured cells that is to be modulated in the methods disclosed may refer to any activity that can be carried out by or in a cultured cell. Examples of activities that may be modulated in the methods disclosed herein include, but are not limited to, differentiation of the cultured cells to cells of a desired lineage, proliferation of the cultured cells (by "proliferation" is meant an increase in cell number or cell size), apoptosis, chemotaxis, receptor binding activity, and enzyme activities. In one embodiment, the activity of the cultured cell is modulated (i.e., increased or decreased) by at least one candidate agent in the methods disclosed herein by at least 20% relative to the activity of a cultured cell that was not exposed to the at least one candidate agent. In other embodiments, the activity of the cultured cell is modulated by at least one candidate agents in the methods disclosed herein by about 1% to about 90%, inclusive, such as 1% to 30%, 10% to 40%, 20% to 50%, 30% to 60%, 40% to 70%, 50% to 80%, and 60% to 90%, inclusive.

In certain embodiments, the present disclosure provides a hollow micropillar array method to screen compounds using epithelial cells cultured on a porous support, enabling the screening of thousands of compounds using a single transwell filter containing cultured cells. Test compounds in an alginate hydrogel may be printed by microinjection in hollow cylindrical micropillars spaced a set distance apart in a particular array configuration such as a square configuration. Compounds may be delivered by positioning the array near the surface of a cell layer, with an interaction gap 112 between the micropillars and cell surface. Micropillar array geometry, and the viscosity of the hydrogel and overlying solutions, may be optimized to produce sustained exposure of cells to test compounds with minimal crosstalk from compounds in neighboring micropillar wells. The methods disclosed herein may be generally applicable for high-content drug screening using small numbers of cells cultured on solid or porous supports.

In one or more embodiments, methods of modulating the cultured cells, specifically to the extent that the cultured cells are under regulation of or is affected by the at least one candidate agent, particularly in response to, e.g. compound release. The term modulating when used in connection with the cultured cells means changing the activity or function of the cultured cells. In other words, the subject methods provide a means for changing the nature of the chemical signals of the cultured cells such that physiological processes associated with the cell functions are modulated or changed.

In certain aspects, the at least one candidate agent modulates an activity of cultured cells. In some embodiments, the cultured cells are cancerous cells. In such embodiments, the at least one candidate agent modulates, for example, the proliferation of the cancerous cells. In other embodiments, the cultured cells are virally-infected cells. In such embodiments, the at least one candidate agent modulates, for example, the viral infection produced as a result of such virally-infected cells. In some other embodiments, the cultured cells have a specific enzyme activity. In such other embodiments, the at least one candidate agent modulates, for example, the specific enzyme activity. In a further embodiment, the cultured cells may be cells that contain receptors in which the ligand binding and/or cell signaling may be modulated. In yet another embodiment, the cultured cells may be any cells that exhibit or is capable of exhibiting a chemotactic response to at least one candidate agent where such cultured cells include, but are not limited to, monocytes, neutrophils and macrophages.

Positioning the Hydrogel in a Lumen of a Hollow Micropillar

In some embodiments, the methods disclosed herein include positioning a hydrogel including at least one candidate agent in a lumen 108 of a hollow micropillar, wherein the hollow micropillar includes a first surface having an open end and a second surface having a closed end in contact with a first substrate 101, wherein the hollow micropillar is orthogonal to the first substrate 101. In certain embodiments, the positioning includes filling the lumen 108 of the hollow micropillar such that a surface of the hydrogel in the lumen 108 is coplanar with the first surface of the hollow micropillar. In other embodiments, the positioning includes filling a portion of the lumen 108 of the hollow micropillar. For example, the positioning includes filling about 5% to about 90% of the lumen 108 of the hollow micropillar, inclusive, such as 5% to 20%, 5% to 30%, 5% to 40%, 5% to 50, 5% to 60%, 5% to 70%, and 5% to 80%, inclusive.

In some embodiments, the positioning includes printing the hydrogel by microinjection in the lumen 108 of the hollow micropillar. Microinjection may be performed using standard techniques known in the art. Printing takes place due to an extremely small interfacial tension and density difference between two aqueous phases. The contact-free printing process ensures that both printed cells and the underlying cell monolayer maintain full viability and functionality. The technique accommodates both arbitrarily shaped patterns and microarrays of cells and bioreagents. The capability to print cells and small molecules on existing cell layers enables unique interrogations of the effects of cell-cell and cell-material interaction on cell fate and function.

In some embodiments, the compounds in a hydrogel are about 1 nL in volume. In other embodiments, the compounds in a hydrogel are about 2 nL in volume. In certain embodiments, the methods described herein enable the printing of about 100 compounds to about 10,000 compounds, inclusive, such as 100 compounds to 500 compounds, 100 compounds to 1000 compounds, 100 compounds to 2000 compounds, 100 compounds to 2500 compounds, 100 compounds to 5,000 compounds, and 100 compounds to 7,500 compounds, inclusive. In some embodiments, the methods described herein enable the printing of about 2,500 compounds. In other embodiments, the methods described herein enable the printing of about 5,000 compounds. Such compounds may be dispensed in the lumen 108 of the hollow micropillar.

Positioning the Hollow Micropillar into Communication with Cultured Cells

In some embodiments, the methods disclosed herein include bringing the first surface of the hollow micropillar into communication with a surface of cultured cells on a second substrate 102 to provide an interaction gap 112 between the first surface of the hollow micropillar and the surface of the cultured cells, wherein the first surface of the hollow micropillar is in a spaced apart and in facing relationship with the surface of cultured cells. In such embodiments, the first substrate 101 may be held parallel to the second substrate 102. In one or more embodiments, the first substrate 101 of the hollow micropillar is held parallel to the second substrate 102 by a force. In some embodiments, the force may be magnetic, electrical, and/or physical.

As described herein, the term "interaction gap" may refer to a space wherein an exchange of compositions may occur. For example, the interaction gap 112 as used herein refers to a space between the first surface of the hollow micropillar and the surface of cultured cells. In some embodiments, the interaction gap 112 has a width of about 5 μm to about 150 μm, inclusive, such as 5 μm to 15 μm, 10 μm to 30 μm, 20 μm to 60 μm, 40 μm to 120 μm, and 80 μm to 150 μm, inclusive. In some embodiments, the interaction gap 112 has a width of 10 μm. In other embodiments, the interaction gap 112 has a width of 5 μm.

In some embodiments, the interaction gap 112 has a width such that crosstalk is reduced between each hollow micropillar in an array configuration. Crosstalk causes interference on adjacent measurement sites. In some embodiments, the number of compounds screened per area of cell culture was maximized with minimal crosstalk from compound in neighboring micropillar wells. In certain embodiments, crosstalk between each hollow micropillar is about 1% to about 50%, inclusive, such as 1% to 10%, 5% to 15%, 10% to 20%, 15% to 25%, 20% to 30%, 25% to 35%, 30% to 40%, 35% to 45%, and 40% to 50%, inclusive. In some embodiments, crosstalk between each hollow micropillar is less than 2%. In other embodiments, crosstalk between each hollow micropillar is reduced by about 1-fold to about 20-fold, inclusive, such as 1-fold to 5-fold, 3-fold to 8-fold, 5-fold to 10-fold, 8-fold to 12-fold, 10-fold to 15-fold, and 13-fold to 18-fold, inclusive. In some other embodiments, crosstalk between each micropillar is reduced by about 2-fold.

In certain embodiments, the first substrate 101 of the hollow micropillar is held parallel to the second substrate 102 by a support device such as a clamp. In such embodiments, the first substrate 101 of the hollow micropillar is directly held parallel to the second substrate 102 such that the first surface of the hollow micropillar having an open end is oriented on the bottom and the second surface having a closed end in contact with the first substrate 101 is oriented on the top. In some embodiments, the support device is a spacer 111 and wherein the spacer 111 is positioned between the first substrate 101 of the hollow micropillar and the second substrate 102. In such embodiments, the spacer 111 has a height greater than the height 105 of the hollow micropillar. In some embodiments, the spacer 111 includes a rectangular shape. Other exemplary shapes of the spacer 111 include a circular shape, cylindrical shape, triangular shape, and the like.

In some embodiments, the spacer 111 has a height that is about 5 μm to 100 μm shorter than the height of a hollow micropillar, inclusive, such as 5 μm to 20 μm, 15 μm to 30 μm, 25 μm to 55 μm, 50 μm to 80 μm, and 75 μm to 100 μm, inclusive. In certain embodiments, the spacer 111 has a height that is about 23 μm shorter than the height 105 of a hollow micropillar.

Adding a Solution to the Interaction Gap

In some embodiments, the methods disclosed herein include adding a solution to the interaction gap 112 such that the at least one candidate agent is released from the hydrogel onto the surface of cultured cells. In some embodiments, the adding includes adding a buffer solution to the interaction gap 112. In certain embodiments, the buffer solution includes phosphate-buffered saline, chloride, and/or iodide.

In one or more embodiments, the present disclosure provides methods involving manual separation of the micropillar array from the cell layer, followed by manual solution addition. In some embodiments, the adding is automated, for example, by using a perfusion system to wash away test compounds and add assay initiators. In some embodiments, the buffer solution is manually added.

In certain embodiments, the solution may include varying concentrations of phosphate-buffered saline. Other exemplary solutions include, but are not limited to, buffers including those containing disodium hydrogen phosphate, sodium chloride and, in some formulations, potassium chloride and potassium dihydrogen phosphate. Some formulations contain magnesium and/or calcium.

In some embodiments, the methods disclosed herein include increasing viscosity of the solution added to the interaction gap 112 such that crosstalk is reduced. In such embodiments, the increasing solution viscosity may include adding methylcellulose to the solution. In some embodiments, solution viscosity may be increased about 1-fold to about 100-fold, inclusive, such as 1-fold to 20-fold, 1-fold to 40-fold, 1-fold to 60-fold, 1-fold to 80-fold, inclusive. In certain embodiments, increasing viscosity of the solution resulted in crosstalk between each hollow micropillar of about 1% to about 25%, inclusive, such as 1% to 5%, 1% to 10%, 1% to 15%, and 1% to 20%, inclusive. In some embodiments, crosstalk between each hollow micropillar is less than 2%. In other embodiments, crosstalk between each hollow micropillar is reduced by about 1-fold to about 5-fold, inclusive, such as 1-fold to 2-fold, 1-fold to 3-fold, and 1-fold to 4-fold, inclusive. In some other embodiments, crosstalk between each micropillar is reduced by about 2-fold.

Measuring a Signal

In some embodiments, the methods disclosed herein include measuring a signal from the cultured cells, wherein the signal indicates whether the at least one candidate agent modulates the activity of the cultured cells. In such embodiments, the methods include determining an amount of the at least one candidate agent released from the hydrogel onto the surface of cultured cells by performing, e.g. mass spectrometry. In certain embodiments, the measuring comprises measuring an optical and/or fluorescent signal.

The measuring may be performed by techniques known in the art. For example, the use of fluorescent molecules in biological research is the standard in many applications. Fluorescent probes are employed to detect protein location and activation, identify protein complex formation and conformational changes and monitor biological processes in vivo. Fluorescent probes may also measure cell shape and intracellular distributions. Such fluorescent molecules respond distinctly to light compared to other molecules. They may absorb light of a specific wavelength and emit light of a different, typically longer, wavelength.

As used herein, mass spectrometry may be used for quantitative elemental analysis, identification of chemical structures and the determination of molecular weight and/or composition of mixtures. Mass spectrometry can be used to ascertain the molecular weights of molecules or the identity of components of a sample based on the detection of a fragmentation pattern of ions produced when the material is ionized. Mass spectrometry involves the formation of ions from analyte molecules, the separation of the various ions according to their mass-to-charge ratio (m/z), and the subsequent generation of a mass spectrum obtained from the separated ions as a result of their having passed through an electric field, a magnetic field or a combination thereof.

The combination of mass spectrometry with liquid chromatography or capillary electrophoresis separation techniques provides a powerful analytical approach to identifying molecular species in a liquid sample. Such systems have the ability to separate solutions containing mixtures of organic or inorganic molecules into liquid fraction effluents containing discrete compounds. In order to analyze the effluents with a mass spectrometer which operates in a high vacuum system, the liquid effluent is generally prepared for ionization and analysis using atmospheric pressure ionization sources such as electrospray and Atmospheric Pressure Chemical Ionization (APCI) sources. When interfaced to mass spectrometers, electrospray and APCI ionization sources can be used to produce ions from continuously flowing liquid samples to provide on-line detection for liquid chromatography separation systems. In some embodiments, the measuring may include performing high-performance liquid chromatography-mass spectrometry (LC/MS).

Utility

A method for screening a candidate agent to determine whether the candidate agent modulates an activity of cultured cells according to the present disclosure finds use in a variety of applications, which are also provided. Applications include research applications; diagnostic applications; industrial applications; and treatment applications. Applications include, e.g., determining the effect (e.g., in a cultured cell) of modulating an activity of the cultured cell; and/or treating an individual by modulating an activity of the cultured cell. The methods, non-transitory computer-readable media, and processor units of the present disclosure find use in a wide variety of contexts, including any context in which it is desirable to modulate an activity of cultured cells.

In some embodiments, a cancer treated by using the present compositions, methods, and systems may be associated with a cancerous cell. The instant methods are useful in the treatment of both primary and metastatic solid tumors, including carcinomas, sarcomas, leukemias, and lymphomas. The methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis and various viral infections such as exanthematous infections, hepatic infections, neurologic infections, hemorrhagic fevers, and cutaneous or mucosal infections; lung diseases such as asthma, chronic obstructive pulmonary disease, chronic bronchitis, emphysema, and acute bronchitis. Of particular interest is the treatment of cystic fibrosis. Associated conditions include exocrine pancreatic insufficiency, impaired bicarbonate and bile acid secretion and aberrant mucus formation, commonly leading to maldigestion and malabsorption, particularly of fat and fat-soluble vitamins. Other complications that may contribute to maldigestion and/or malabsorption include small intestine bacterial overgrowth, enteric circular muscle dysfunction, abnormal intestinal mucus, and intestinal inflammation.

In some embodiments, activity modulated may be an enzymatic activity including, but not limited to, noncovalent interactions such as polymerization and depolymerization and/or covalent interactions such as synthesis or degradation. For example, modulation of the activity of a pancreatic enzyme encompasses any change in the activity of the pancreatic enzyme, including, but not limited to, the decrease in the activity of the pancreatic enzyme (e.g., complete, or substantially complete, inhibition of the activity of the pancreatic enzyme). The modulation of the activity of the pancreatic enzyme in vitro, may also cause a significant improvement in a phenotype, in vivo, associated with, for example, cystic fibrosis (e.g., the agent causes one or more of the following changes: raises bicarbonate and bile acid secretion, lowers mucus formation, gain and maintain healthy weight, digest carbohydrates, proteins and fats, and/or absorb essential nutrients such as vitamins and minerals).

Systems

As summarized above, the systems disclosed herein provide an approach of screening a candidate agent to determine whether the candidate agent modulates an activity of cultured cells, including a hollow micropillar, wherein a hydrogel comprising at least one candidate agent is positioned in a lumen of the hollow micropillar, wherein the hollow micropillar comprises a first surface having an open end and a second surface having a closed end in contact with a first substrate, wherein the hollow micropillar is orthogonal to the first substrate; a plurality of cultured cells, wherein the first surface of the hollow micropillar is in communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells; a solution, wherein the solution is added to the interaction gap such that the at least one candidate agent is released from the hydrogel onto the surface of cultured cells; a processor unit; and a non-transitory computer-readable storage medium comprising instructions, which when executed by the processor unit, cause the processor unit to measure a signal from the cultured cells, wherein the signal indicates whether the at least one candidate agent modulates the activity of the cultured cells.

In some embodiments, the non-transitory computer-readable storage medium comprises instructions, which when executed by the processor unit, cause the processor unit to determine an amount of the at least one candidate agent released from the hydrogel onto the surface of the plurality of cultured cells. In such embodiments, the processor unit may be a mass spectrometer.

In some embodiments, the non-transitory computer-readable storage medium comprises instructions, which when executed by the processor unit, cause the processor unit to measure an optical signal. In other embodiments, the non-transitory computer-readable storage medium comprises instructions, which when executed by the processor unit, cause the processor unit to measure a fluorescent signal.

In further embodiments, the system includes increasing viscosity of the solution added to the interaction gap such that crosstalk is reduced. In such embodiments, increasing solution viscosity comprises adding methylcellulose to the solution. In some embodiments, solution viscosity may be increased about 1-fold to about 100-fold, inclusive, such as 1-fold to 20-fold, 1-fold to 40-fold, 1-fold to 60-fold, 1-fold to 80-fold, inclusive. In certain embodiments, increasing viscosity of the solution resulted in crosstalk between each hollow micropillar of about 1% to about 25%, inclusive, such as 1% to 5%, 1% to 10%, 1% to 15%, and 1% to 20%, inclusive. In some embodiments, crosstalk between each hollow micropillar is less than 2%. In other embodiments, crosstalk between each hollow micropillar is reduced by about 1-fold to about 5-fold, inclusive, such as 1-fold to 2-fold, 1-fold to 3-fold, and 1-fold to 4-fold, inclusive. In some other embodiments, crosstalk between each micropillar is reduced by about 2-fold.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-100 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of screening a candidate agent to determine whether the candidate agent modulates an activity of cultured cells, the method comprising:

positioning a hydrogel comprising at least one candidate agent in a lumen of a hollow micropillar, wherein the hollow micropillar comprises a first surface having an open end and a second surface having a closed end in contact with a first substrate, wherein the hollow micropillar is orthogonal to the first substrate;

bringing the first surface of the hollow micropillar into communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells;

adding a solution to the interaction gap such that the at least one candidate agent is released from the hydrogel onto the surface of cultured cells; and measuring a signal from the cultured cells, wherein the signal indicates whether the at least one candidate agent modulates the activity of the cultured cells.

2. The method of aspect 1, wherein the hydrogel comprises alginate.

3. The method of aspect 1 or 2, wherein the at least one candidate agent comprises at least two candidate agents.

4. The method of aspect 1 or 2, wherein the at least one candidate agent comprises at least one thousand candidate agents.

5. The method of any one of aspects 1-4, wherein the positioning comprises filling the lumen of the hollow micropillar such that a surface of the hydrogel in the lumen is coplanar with the first surface of the hollow micropillar.

6. The method of any one of aspects 1-5, wherein the positioning comprises filling a portion of the lumen of the hollow micropillar.

7. The method of any one of aspects 1-6, wherein the positioning comprises printing the hydrogel by microinjection in the lumen of the hollow micropillar.

8. The method of any one of aspects 1-7, wherein the hollow micropillar comprises an inner diameter and an outer diameter.

9. The method of aspect 8, wherein the inner diameter is 50-600 microns.

10. The method of aspect 8, wherein the outer diameter is 60-900 microns.

11. The method of any one of aspects 1-10, wherein the hollow micropillar comprises a coating layer.

12. The method of aspect 11, wherein the coating layer is hydrophilic.

13. The method of any one of aspects 1-12, wherein the hollow micropillar has a height of 150 microns.

14. The method of any one of aspects 1-13, wherein the first substrate comprises polydimethylsiloxane.

15. The method of any one of aspects 1-14, wherein the cultured cells comprise non-epithelial cells.

16. The method of any one of aspects 1-14, wherein the cultured cells comprise epithelial cells.

17. The method of aspect 16, wherein the cultured cells comprise filter-grown epithelial cells.

18. The method of aspect 16, wherein the epithelial cells express the cystic fibrosis transmembrane conductance regulator chloride (CFTR) channel.

19. The method of any of aspects 1-18, wherein the first surface of the hollow micropillar is in a spaced apart and in facing relationship with an apical surface of the cultured cells.

20. The method of any one of aspects 1-19, wherein the second substrate comprises polydimethylsiloxane.

21. The method of any one of aspects 1-20, wherein the interaction gap has a width of 10 microns.

22. The method of any one of aspects 1-20, wherein the interaction gap has a width of 5 microns.

23. The method of any one of aspects 1-22, wherein the first substrate is held parallel to the second substrate.

24. The method of aspect 23, wherein the first substrate of the hollow micropillar is held parallel to the second substrate by a force.

25. The method of aspect 24, wherein the force is a magnetic force.

26. The method of aspect 24, wherein the force is an electrical force.

27. The method of any one of aspects 1-26, wherein the first substrate of the hollow micropillar is held parallel to the second substrate by a support device.

28. The method of aspect 27, wherein the support device is a clamp.

29. The method of aspect 27, wherein the support device is a spacer and wherein the spacer is positioned between the first substrate of the hollow micropillar and the second substrate.

30. The method of aspect 29, wherein the spacer has a height greater than the height of the hollow micropillar.

31. The method of aspect 29 or 30, wherein the spacer comprises a rectangular shape.

32. The method of any one of aspects 1-31, wherein the adding comprises adding a buffer solution to the interaction gap.

33. The method of aspect 32, wherein the buffer solution comprises phosphate-buffered saline.

34. The method of aspect 32 or 33, wherein the buffer solution comprises chloride.

35. The method of aspect 32 or 33, wherein the buffer solution comprises iodide.

36. The method of any one of aspects 32-35, wherein the buffer solution is manually added.

37. The method of aspect 1, the method further comprising determining an amount of the at least one candidate agent released from the hydrogel onto the surface of cultured cells.

38. The method of aspect 37, wherein the determining comprises performing mass spectrometry.

39. The method of any one of aspects 1-38, wherein the measuring comprises measuring an optical signal.

40. The method of any one of aspects 1-38, wherein the measuring comprises measuring a fluorescent signal.

41. The method of any one of aspects 1-40, wherein the first substrate is in contact with a plurality of hollow micropillars.

42. The method of aspect 41, wherein the plurality of hollow micropillars comprises two or more hollow micropillars.

43. The method of aspect 41, wherein the plurality of hollow micropillars comprises three or more hollow micropillars.

44. The method of any one of aspects 41-43, wherein the hydrogel comprising the at least one candidate agent is positioned in the lumen of each hollow micropillar of the plurality of hollow micropillars.

45. The method of any one of aspects 41-44, wherein each hollow micropillar is positioned at a set distance apart such that crosstalk between each hollow micropillar is reduced.

46. The method of aspect 45, wherein crosstalk between each hollow micropillar is less than 2%.

47. The method of aspect 45 or 46, wherein the set distance is the same between each hollow micropillar.

48. The method of any one of aspects 45-47, wherein the set distance is 100-1000 microns.

49. The method of any one of aspects 1-48, the method further comprising increasing viscosity of the solution added to the interaction gap such that crosstalk is reduced.

50. The method of aspect 49, wherein the increasing viscosity comprises adding methylcellulose to the solution.

51. A system of screening a candidate agent to determine whether the candidate agent modulates an modulate activity of cultured cells, the system comprising:
    a hollow micropillar, wherein a hydrogel comprising at least one candidate agent is positioned in a lumen of the hollow micropillar, wherein the hollow micropillar comprises a first surface having an open end and a second surface having a closed end in contact with a first substrate, wherein the hollow micropillar is orthogonal to the first substrate;

a plurality of cultured cells, wherein the first surface of the hollow micropillar is in communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells;

a solution, wherein the solution is added to the interaction gap such that the at least one candidate agent is released from the hydrogel onto the surface of cultured cells;

a processor unit; and a non-transitory computer-readable storage medium comprising instructions, which when executed by the processor unit, cause the processor unit to measure a signal from the cultured cells, wherein the signal indicates whether the at least one candidate agent modulates the activity of the cultured cells.

52. The system of aspect 51, wherein the hydrogel comprises alginate.

53. The system of aspect 51 or 52, wherein the at least one candidate agent comprises at least two candidate agents.

54. The system of aspect 51 or 52, wherein the at least one candidate agent comprises at least one thousand candidate agents.

55. The system of any one of aspects 51-54, wherein the hydrogel comprising the at least one candidate agent fills the lumen of the hollow micropillar such that a surface of the hydrogel in the lumen is coplanar with the first surface of the hollow micropillar.

56. The system of any one of aspects 51-54, wherein the hydrogel comprising the at least one candidate agent fills a portion of the lumen of the hollow micropillar.

57. The system of any one of aspects 51-56, wherein the hydrogel comprising the at least one candidate agent is printed by microinjection in the lumen of the hollow micropillar.

58. The system of any one of aspects 51-57, wherein the hollow micropillar comprises an inner diameter and an outer diameter.

59. The system of aspect 58, wherein the inner diameter is 50-600 microns.

60. The system of aspect 58, wherein the outer diameter is 60-900 microns.

61. The system of any one of aspects 51-60, wherein the hollow micropillar comprises a coating layer.

62. The system of aspect 61, wherein the coating layer is hydrophilic.

63. The system of any one of aspects 51-62, wherein the hollow micropillar has a height of 150 microns.

64. The system of any one of aspects 51-63, wherein the first substrate comprises polydimethylsiloxane.

65. The system of any one of aspects 51-64, wherein the plurality of cultured cells comprises non-epithelial cells.

66. The system of any one of aspects 51-64, wherein the plurality of cultured cells comprises epithelial cells.

67. The system of aspect 66, wherein the plurality of cultured cells are filter-grown epithelial cells.

68. The system of aspect 66, wherein the epithelial cells express the cystic fibrosis transmembrane conductance regulator chloride (CFTR) channel.

69. The system of any of aspects 51-68, wherein the first surface of the hollow micropillar is in a spaced apart and in facing relationship with an apical surface of the cultured cells.

70. The system of any one of aspects 51-69, wherein the second substrate comprises polydimethylsiloxane.

71. The system of any one of aspects 51-70, wherein the interaction gap has a width of 10 microns.

72. The system of any one of aspects 51-70, wherein the interaction gap has a width of 5 microns.

73. The system of any one of aspects 51-72, wherein the first substrate is held parallel to the second substrate.

74. The system of any one of aspects 73, wherein the first substrate of the hollow micropillar is held parallel to the second substrate by a force.

75. The system of aspect 74, wherein the force is a magnetic force.

76. The system of aspect 74, wherein the force is an electrical force.

77. The system of any one of aspects 51-76, wherein the first substrate of the hollow micropillar is held parallel to the second substrate by a support device.

78. The system of aspect 77 wherein the support device is a clamp.

79. The system of aspect 77, wherein the support device is a spacer and wherein the spacer is positioned between the first substrate of the hollow micropillar and the second substrate.

80. The system of aspect 79, wherein the spacer has a height greater than the height of the hollow micropillar.

81. The system of aspect 79 or 80, wherein the spacer comprises a rectangular shape.

82. The system of any one of aspects 51-81, wherein the solution added to the interaction gap is a buffer solution.

83. The system of aspect 82, wherein the buffer solution comprises phosphate-buffered saline.

84. The system of aspect 82 or 83, wherein the buffer solution comprises chloride.

85. The system of aspect 82 or 83, wherein the buffer solution comprises iodide.

86. The system of any one of aspects 82-85, wherein the buffer solution is manually added.

87. The system of aspect 51, wherein the non-transitory computer-readable storage medium comprises instructions, which when executed by the processor unit, cause the processor unit to determine an amount of the at least one candidate agent released from the hydrogel onto the surface of the plurality of cultured cells.

88. The system of aspect 87, wherein the processor unit is a mass spectrometer.

89. The system of any one of aspects 51-88, wherein the non-transitory computer-readable storage medium comprises instructions, which when executed by the processor unit, cause the processor unit to measure an optical signal.

90. The system of any one of aspects 51-88, wherein the non-transitory computer-readable storage medium comprises instructions, which when executed by the processor unit, cause the processor unit to measure a fluorescent signal.

91. The system of any one of aspects 51-90, wherein the first substrate is in contact with a plurality of hollow micropillars.

92. The system of aspect 91, wherein the plurality of hollow micropillars comprises two or more hollow micropillars.

93. The system of aspect 92, wherein the plurality of hollow micropillars comprises three or more hollow micropillars.

94. The system of any one of aspects 91-93, wherein the hydrogel comprising the at least one candidate agent is positioned in the lumen of each hollow micropillar of the plurality of hollow micropillars.

95. The system of any one of aspects 91-94, wherein each hollow micropillar is positioned at a set distance apart such that crosstalk between each hollow micropillar is reduced.

96. The system of aspect 95, wherein crosstalk between each hollow micropillar is less than 2%.

97. The system of aspect 95 or 96, wherein the set distance is the same between each hollow micropillar.

98. The system of any one of aspects 95-97, wherein the set distance is 100-1000 microns.

99. The system of any one of aspects 51-98, the system further comprising increasing viscosity of the solution added to the interaction gap such that crosstalk is reduced.

100. The system of aspect 99, wherein increasing viscosity comprises adding methylcellulose to the solution.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

The following materials and methods generally apply to the results presented in the Examples described herein except where noted otherwise.

Fabrication of Hollow Micropillar Arrays

A hollow micropillar array was fabricated to print 100 compounds in a 3×3 mm² area, where about a 23 μm-high rectangular spacer was fabricated to set about a 10 μm gap between the upper surface of micropillars and the cell layer (assuming about a 15 μm cell height). The hollow micropillar array was fabricated using conventional double layer soft-lithography, as diagrammed and detailed in FIG. 3.

Hollow micropillar array fabrication used conventional double layer soft-lithography. Fabrication of the first (10-μm spacer) layer (FIG. 3, left) included dropping 4 ml SU-82015 (MicroChem, Westborough, MA) on a 4-inch diameter silicon wafer (Addison Engineering) and spin-coating at 500 rpm for 10 s, and then at 2000 rpm for 30 s to give about a 23 μm thickness, and then prebaking at 95° C. for 3 min. The photoresist was then exposed to UV light (350 nm, 140 mJ/cm²) through a previously prepared film mask and post-baked at 95° C. for 4 min. The final spacer features on the silicon wafer were developed using SU-8 developer (MicroChem Corp.) for 3 min, following isopropyl alcohol treatment for 3 min and rinsing with deionized water for 3 min. After drying with N₂, the wafer was placed on a hotplate for 1 h. The channel height of the master was measured using a profilometer (XP-2 stylus profilometer, Ambios Technology, Inc.).

Fabrication of the second (150-μm hollow micropillar) layer (FIG. 3, center) included dropping 4 ml SU-8 2100 on the first layer and spin-coating at 500 rpm for 10 s and then at 1550 rpm for 30 s to give about a 150 μm thickness, and then prebaking at 65° C. for 5 min and at 95° C. for 30 min. The photoresist was then exposed to UV light (350 nm, 260 mJ/cm²) by aligning the first layer with the second layer mask through align keys. After post-baking at 65° C. for 5 min and then at 95° C. for 12 min, the final features on the silicon wafer were developed using SU-8 developer for 30 min, followed by 5 min of isopropyl alcohol treatment and rising with deionized water for 5 min and drying with N₂.

Figure 3:
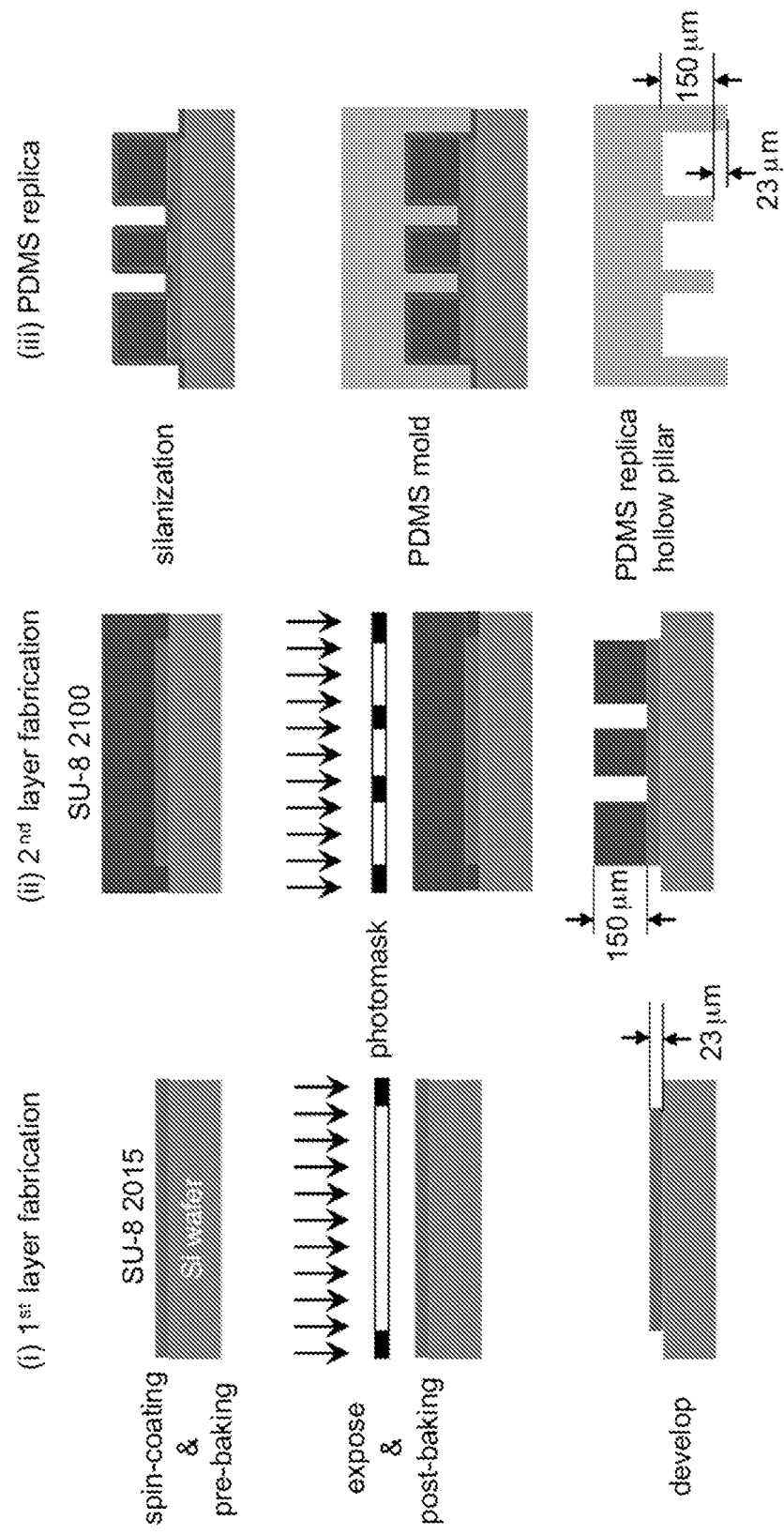
FIG. 3 depicts a schematic showing of hollow micropillar array fabrication.

The silanization and PDMS replica mold was created as shown in FIG. 3, right. The fabricated SU-8 master surface was silanized to prevent PDMS mold adherence to the master and to facilitate release the PDMS from the master. Two drops of the silanizing agent (trichloro(1H,1H,2H,2H-perfluorooctyl)silane, Sigma) in an Eppendorf tube was placed in a vacuum desiccator to allow monolayer formation on the surface of the master. The SU-8 wafer was placed overnight next to the Eppendorf tube. Finally, the wafer was placed on a hotplate at 150° C. for 10 min to cure and evaporate excess silane. The PDMS hollow micropillar was fabricated by standard replica molding using DA-184A and DA-184B (Dow Corning) in a 10:1 ratio. Liquid PDMS was poured on the master and air bubbles in the deep structure were eliminated under vacuum for 1 h, and cured at 80° C. for 30 min. The wafer was refrigerated at 4° C. for 30 min to shrink the microstructure before peeling the PDMS stamp from the silicon wafer in order to prevent disruption during peeling.

The structured PDMS layer was treated with air plasma (PlasmaFlo PDC-FMG and Plasma cleaner, PDC-32G Harrick Plasma, Ithaca, NY) at 700 mTorr for 90 min. Just after the plasma treatment the PDMS layer was submerged in a polyethylene glycol (PEG) solution (molecular weight 200, Sigma-Aldrich, St. Louis, MO) and the PDMS surface was coated for 30 min to make a hydrophilic surface to facilitate compound printing in the hollow micropillars. The PEG-coated PDMS channel was washed with deionized water and dried with N₂ gas for 1 h at room temperature. The PEG coating quality was confirmed by measuring the contact angle on the PDMS surface, which was roughly 110° for untreated PDMS and roughly 20° for PEG-coated PDMS.

Compound Microprinting

Compounds (roughly a 1 nL volume) in an alginate solution (alginic acid sodium salt from brown algae, Sigma-Aldrich) were printed in each hollow micropillar well using microdispensing technology (sciFLEXARRAYER S3, Scienion, Berlin, Germany) First, 1 nL of 0.2% $CaCl_2$ was printed in each well and dried completely for 30 min at room temperature. Then, 1 nL of a 1% alginate solution containing 25 μM test compound (from DMSO stock) was microdispensed in the hollow micropillar well, with a final DMSO concentration of 5%. The test compound/alginate mixture gelled within a few minutes. After printing, the hollow pillar array was kept in a humidified chamber (tape-sealed Petri dish lined with water-soaked tissue paper) to prevent evaporation.

Mathematical Modeling of Compound Diffusion

Cross-talk was analyzed by mathematical modeling of compound diffusion using Comsol Multiphysics (version 3.4; Comsol Inc., Burlington, MA). Compound diffusion in the 3-dimensional hollow micropillar array is described by the following diffusion equation: $\partial C/\partial t = -DV^2 C$, where C is compound concentration, t is the time and D is compound diffusion coefficient.

Figure 4A:
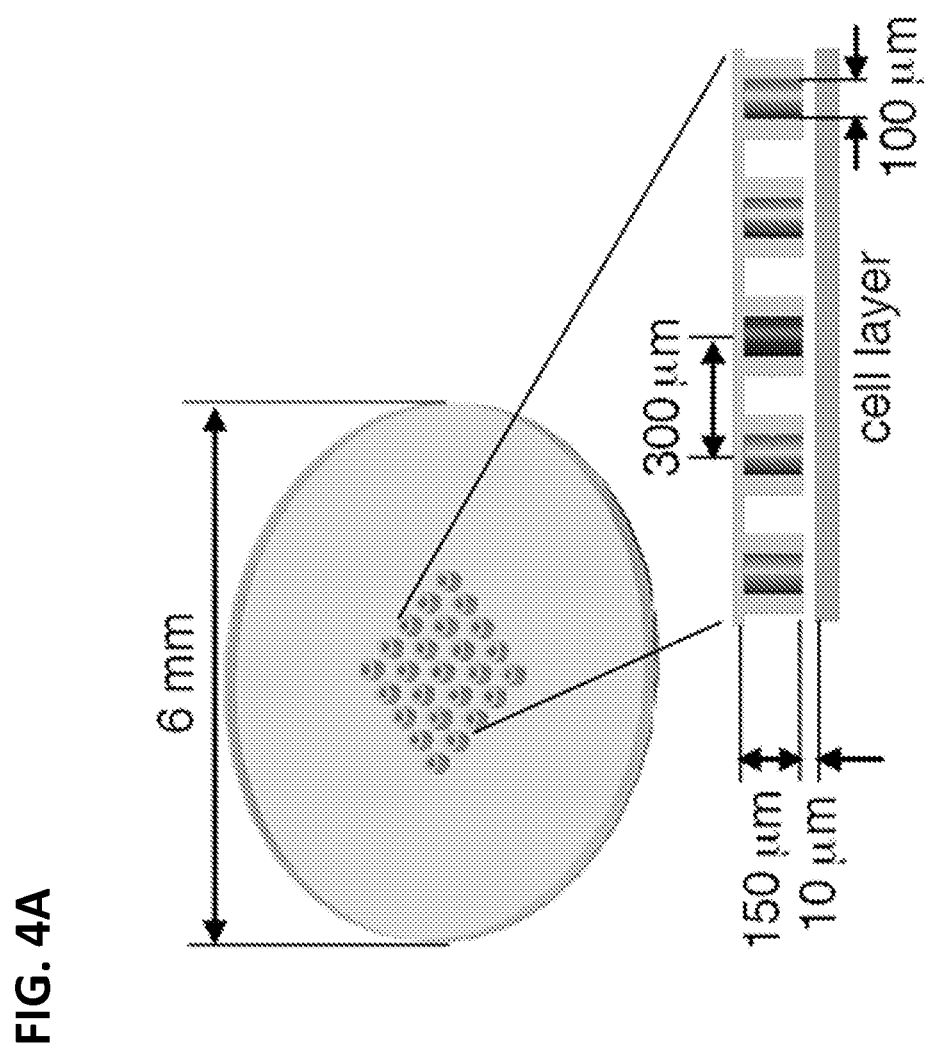
FIG. 4A-4C depict a computational modeling of cell exposure to compounds released from hollow micropillars.
Figure 5:
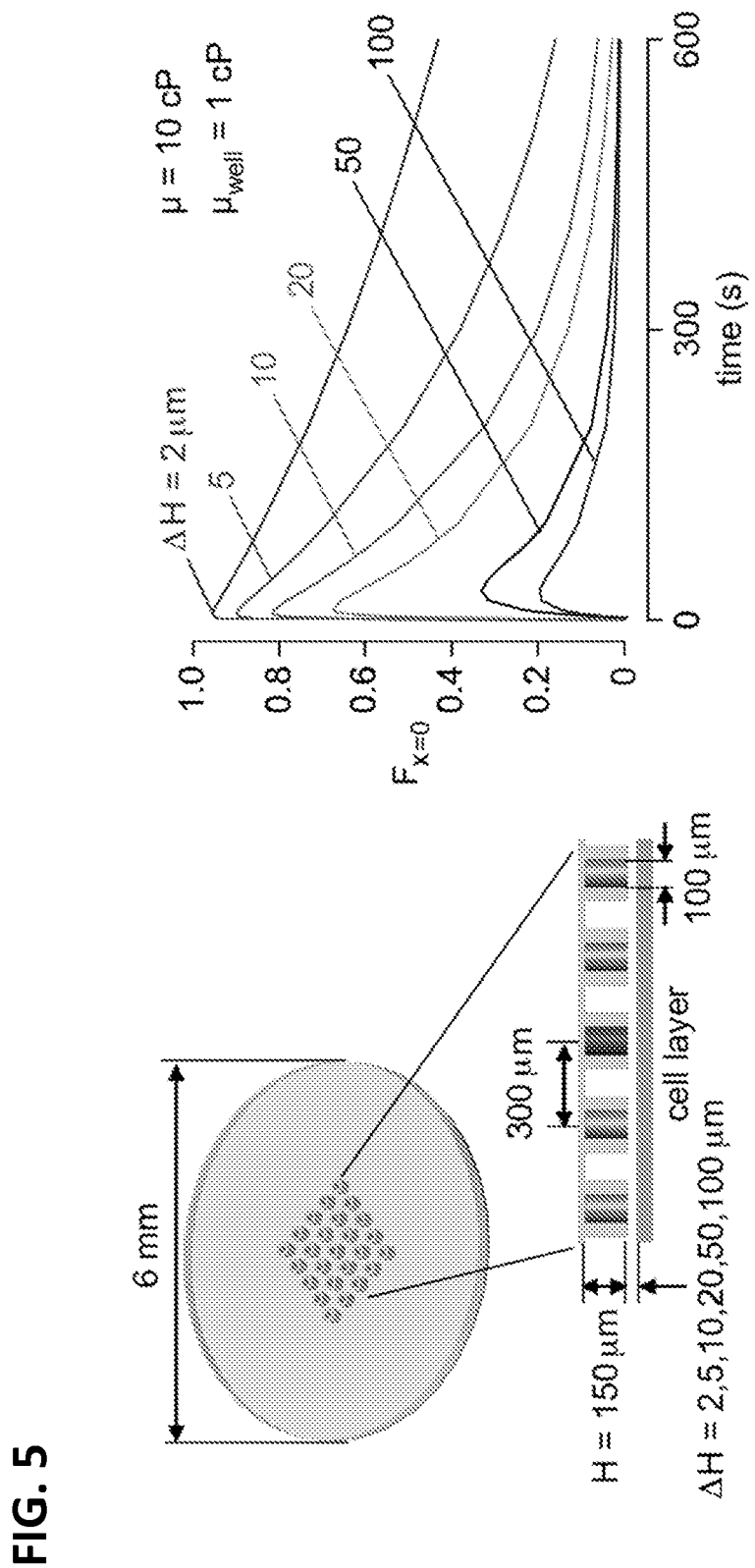
FIG. 5 depicts a computational modeling of cell exposure to compounds released from hollow micropillars for different gap distances between the cell surface and the hollow micropillar

The computational domain was a 6-mm diameter disk with 160-μm height containing a 5×5 hollow micropillar array (FIG. 4A). Micropillars were 100 μm in diameter and 150 µm in height, with 300-µm gap between micropillars. Different distances between the micropillar upper surface and the cell layer were modeled (2, 5, 10, 20, 50 and 100 µm) (FIG. 5, left). Compound concentration at the cell surface of the central hollow micropillar relative to that in the well ($F_x=0$) for indicated ΔH and solution viscosity of 10 cP demonstrated that reduced ΔH was associated with more stable cell exposure to compound (FIG. 5, right).

As the initial condition, the cylindrical hollow micropillar well contained uniformly distributed test compound (concentration C) with zero concentration elsewhere. Compound diffusion coefficient (D), which is related to solution viscosity by the Stokes-Einstein equation, $D=k_B T/(6\pi\eta r)$, was varied between $10^{-9}$ m²/s and $10^{-11}$ m²/s, corresponding to diffusion in water (1 cP) and a viscous 100 cP solution. Impermeant boundary conditions were applied at the hollow micropillar surface and the cell layer, and a non-reflective boundary condition was applied at the outer boundary.

Fluorescent Dye Diffusion Measurements

For testing diffusion, a polar fluorescent dye (10 µM sulforhodamine 101, 490 daltons, Sigma-Aldrich) was printed together with test compounds (in alginate hydrogel) in a subset of microwells. Dye diffusion following array attachment to a glass plate or cell layer was measured by fluorescence confocal microscopy using a 4× lens.

Compound Release from Alginate Hydrogels

Compound release from alginate hydrogels was determined using high-performance liquid chromatography-mass spectrometry (LC/MS). 20 µl of 0.2% CaCl₂ was added in a 96-well plate, dried, and a 10-µM concentration of test compounds in 20 µl of 1% alginate solution was added in the CaCl₂-containing wells. After alginate gelation, 200 µl of PBS was added to each well and kept in room temperature for 3 hours. 200 µl of the PBS solution was collected at specified time points, mixed with 500 µl of ethyl acetate, and centrifuged for 15 min at 3000 rpm. The organic layer was used for LC/MS analysis. HPLC was done on an Xterra MS C18 column (2.1 mm×100 mm, 3.5 µm) with 0.2 mL/min water/acetonitrile (containing 0.1% formic acid), 25 min linear gradient, 5-95% acetonitrile.

Iodide Transport in CFTR-Expressing FRT Cells

FRT cells stably expressing human wildtype CFTR and yellow fluorescent protein YFP-H148/I152L were cultured on polyester transwell filters until they formed a tight monolayer (electrical resistance >3 kOhm·cm²), as previously described in the art. The cell culture medium was then replaced with a viscous solution consisting of 2% methylcellulose (about 41,000 daltons, Sigma-Aldrich) in PBS. The cell layer was contacted with a 10×10 micropillar array for 10 min, and then the viscous solution was rinsed. For transport measurement, an iodide-containing solution (PBS with 120 mM chloride was replaced by iodide) was added manually on top of the cell layer. YFP fluorescence of the entire cell culture area was monitored for 5 min at 10 Hz using a 2× magnification lens (CFI Plan Apo Lambda 2X, Nikon, Melville, NY) with EMCCD camera detector (C9100, Hamamatsu). YFP fluorescence is reduced as the added extracellular iodide is transported into cell cytoplasm through activated CFTR. The time course of fluorescence for each of the 100 locations, each integrated over the 100-µm diameter circular cell area overlying the corresponding micropillar well, was determined using ImageJ. A specified subset of hollow micropillars contained the CFTR agonist forskolin (10 µM in alginate hydrogel).

Results

Example 1: Design of Hollow Micropillar Array

Figure 2B:
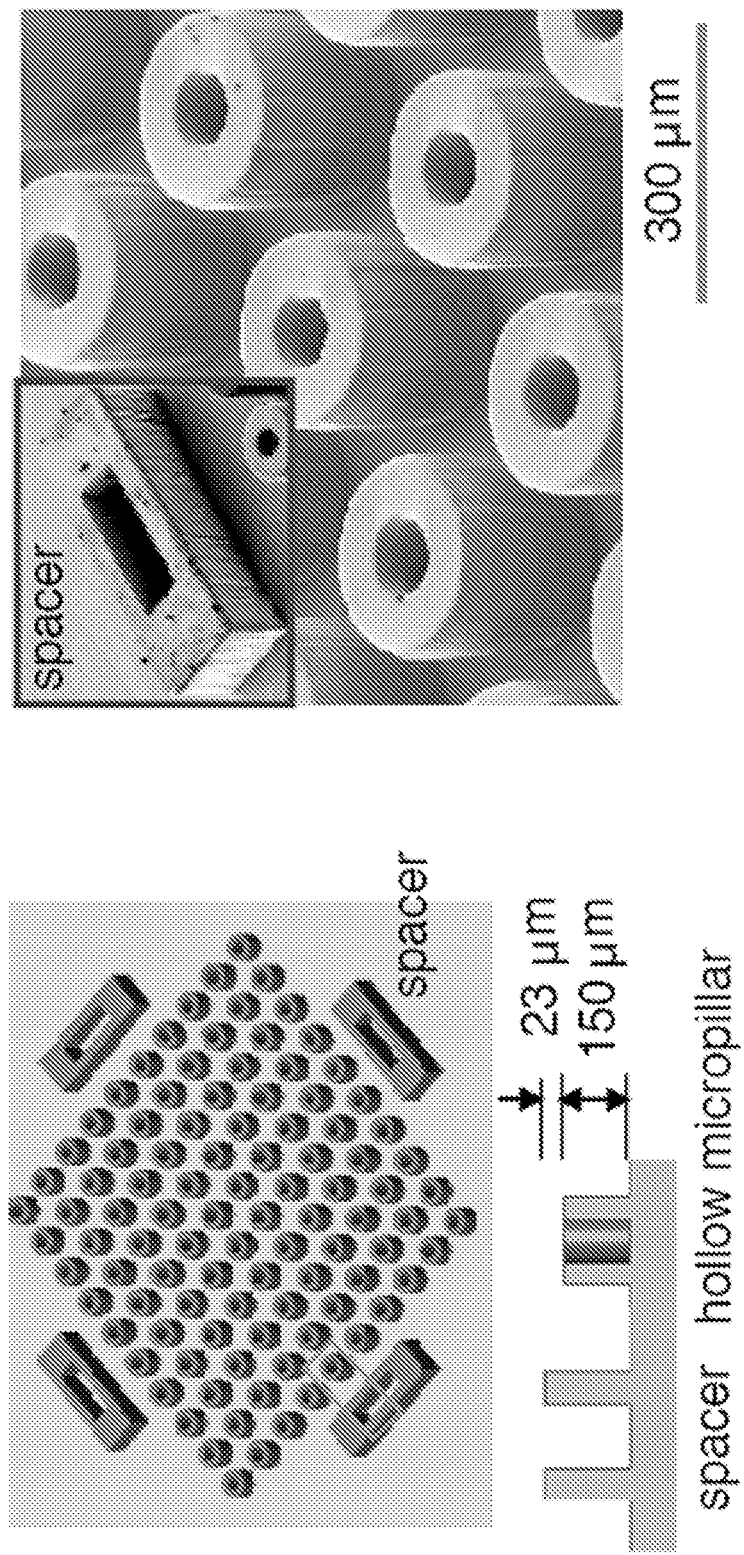

The design criteria for the hollow micropillar array included feasibility of fabrication, and a high micropillar density in which cells in the vicinity of micropillars were exposed to a sustained concentration of test compound with minimal cross-talk from compounds in neighboring wells and without direct contact or damage to the cell layer. In addition to challenges in specifying micropillar geometry and density to accomplish these goals was the need to establish a hydrogel vehicle and a PDMS treatment to stably retain and release compounds from the hollow micropillars. As shown in FIG. 2A-2B, compounds were printed in a dense square array of hollow micropillars that contacted the apical-facing surface of an epithelial cell monolayer. Micropillar and contact geometry, and solution viscosities, were optimized to produce sustained local exposure of cells to test compounds for up to tens of minutes, with minimal crosstalk from compounds in neighboring micropillar wells.

A hollow micropillar array was designed to print about 2500 compounds in about a 1.5×1.5 cm² area as shown in FIG. 2A (left), which would allow testing of about 5000 compounds on a standard 24-mm diameter porous filter containing a monolayer of cultured cells. The dense micropillar array consisted of 100 µm inner diameter, cylindrical hollow micropillars spaced 300 µm apart as shown in FIG. 2A (right), so that about 20 cells of typical size would overlie the hollow area of each micropillar. Compounds were dispensed in the hollow cylindrical volume of micropillars. Following compound incubation the micropillar array was separated from the cell layer and a fluorescence-based assay initiated, in which compound identity was determined from cell position. For initial design optimization, various hollow micropillar designs (inner diameters: 100, 150 and 200 µm, with different heights) were tested for feasibility of fabrication and compound printing, and modeled computationally to confirm compound exposure to cells with minimal cross-talk.

Following design optimization as described herein, the hollow micropillar array described herein was fabricated to print 100 compounds in a 3×3 mm² area as shown in FIG. 2B (left), in which a 23 µm spacer was fabricated to set about a 10 µm gap between the upper surface of micropillars and the cell layer. As shown in FIG. 2B (right), a scanning electron micrograph of the fabricated hollow micropillar array shows the cylindrical wells in each micropillar and a rectangular spacer. Test compounds (about 1 nL of 20 µM stock in hydrogel) were printed by microinjection in each hollow micropillar. The micropillars were spaced 300 µm apart so that the whole array was a 3 mm square. The array made contact for 10-15 min with the apical surface of a filter-grown epithelial cell layer, with 5-10 µm gap spacing between the upper surface of the micropillar and the cell apical membrane. For the preliminary studies, the micropillar array was handled magnetically and solution exchange was manual.

The results herein provided proof of concept for a high-content drug screening approach involving compound release from hydrogels printed in cylindrical microwells in close contact with a monolayer cell culture. The hollow micropillar array design with hydrogel-embedded compounds and viscous aqueous solution between the micropillars and cell layer satisfied the specified screening criteria, which included exposure of cells to test compound for up to tens of minutes with minimal cross-talk, and efficient compound retention and release from hydrogels. Specification of the various parameters, including micropillar geometry and density, hydrogel composition and solution viscosity, involved trade-offs between compound density, cell exposure time to test compounds, and cross-talk from compounds in neighboring wells. Varying of the parameters, for example increasing viscosity and altering micropillar geometry such as reducing micropillar diameter, would allow for a substantially increased compound density as needed. The computational modeling presented in FIGS. 2A-2B, FIG. 5, FIG. 7 and FIG. 8 show the predicted interplay among the parameters with regard to compound exposure and cross-talk, and provides proof of concept for the parameter selections herein. A particular design feature, as modeled mathematically and validated experimentally, was the hollow, long micropillar design, which allowed retention of adequate compound amounts for sustained release, and slowed lateral diffusion of compounds following their release.

The parameters optimized included the geometry of the hollow micropillars (inner and outer diameters, height), the spacing between the hollow micropillars, the composition and viscosity of the compound-containing hydrogel that filled the micropillars, the composition and viscosity of the solution overlying the micropillar layer, and the gap spacing between the top of the micropillars and the cell layer. The goal was to enable contact of test compounds with nearby cells for tens of minutes without cross-talk, and with a sufficiently high density of micropillars for screening of thousands of compounds in a single measurement. Additional considerations included selection of a hydrogel for efficient compound release, without surface adsorption, and which was suitable for up to many-months storage of pre-printed micropillar arrays.

Example 2: Computational Modeling of Hollow Micropillar Array

A particular design criterion for high-content compound screening was maximizing the number of compounds screened per area of cell culture with minimal cross-talk from compound in neighboring micropillar wells. A typical small molecule with diffusion coefficient ($D \approx 10^{-9}$ m$^2$/s) diffuses about 1.5 mm during a 10-min incubation according to simple theoretical analysis $x \approx (4Dt)^{1/2}$, where x is diffusion distance and t is diffusion time.

Two approaches were implemented in order to minimize cross-talk and increase compound array density: increased viscosity of (i) solution overlying cells; and (ii) a hollow pillar microstructure. Increased solution viscosity reduced compound diffusion coefficient according to Stokes-Einstein equation, $D=k_B T/(6\pi\eta r)$, where D is diffusion coefficient, $k_B$ Boltzmann's constant, T absolute temperature, $\eta$ solution viscosity, and r particle radius. Solution viscosity was increased experimentally using methylcellulose. A hollow micropillar geometry provided a reservoir to contain test compounds and reduced cross-talk because of compound dilution into the space between neighboring micropillar wells. The micropillar geometry (with troughs between micropillars), and with a relatively viscous (10-50 cP) overlying solution layer, were important factors in producing sustained compound exposure to the cell layer locally, without exposure to cells overlying neighboring micropillar wells.

Figure 4B:
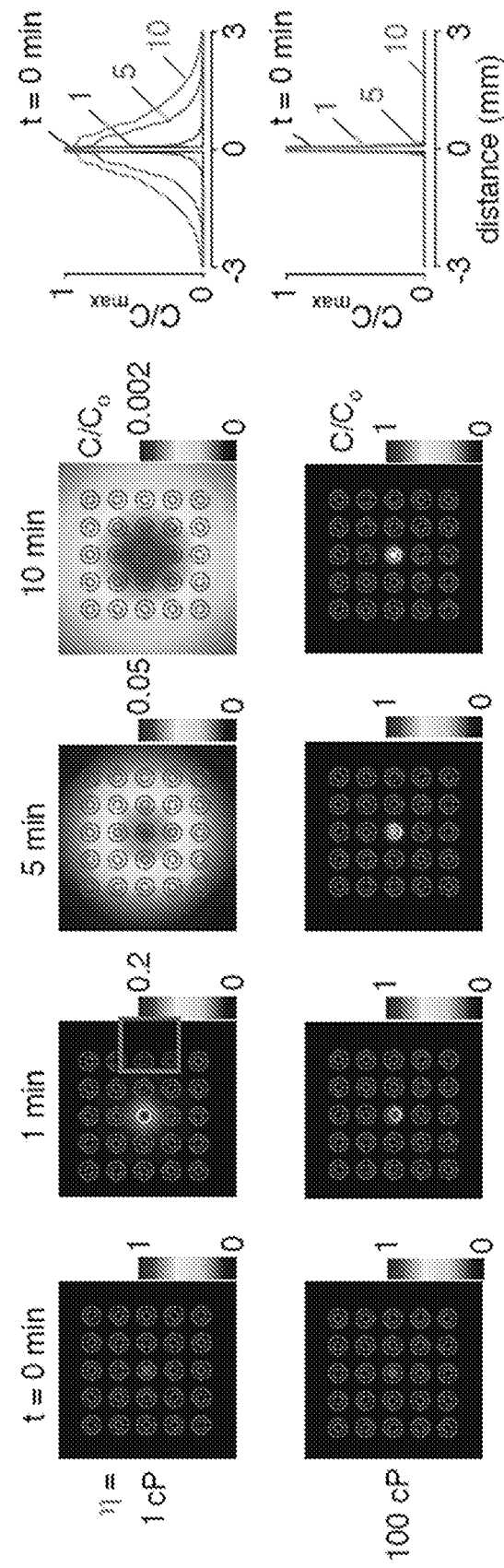
Figure 4C:
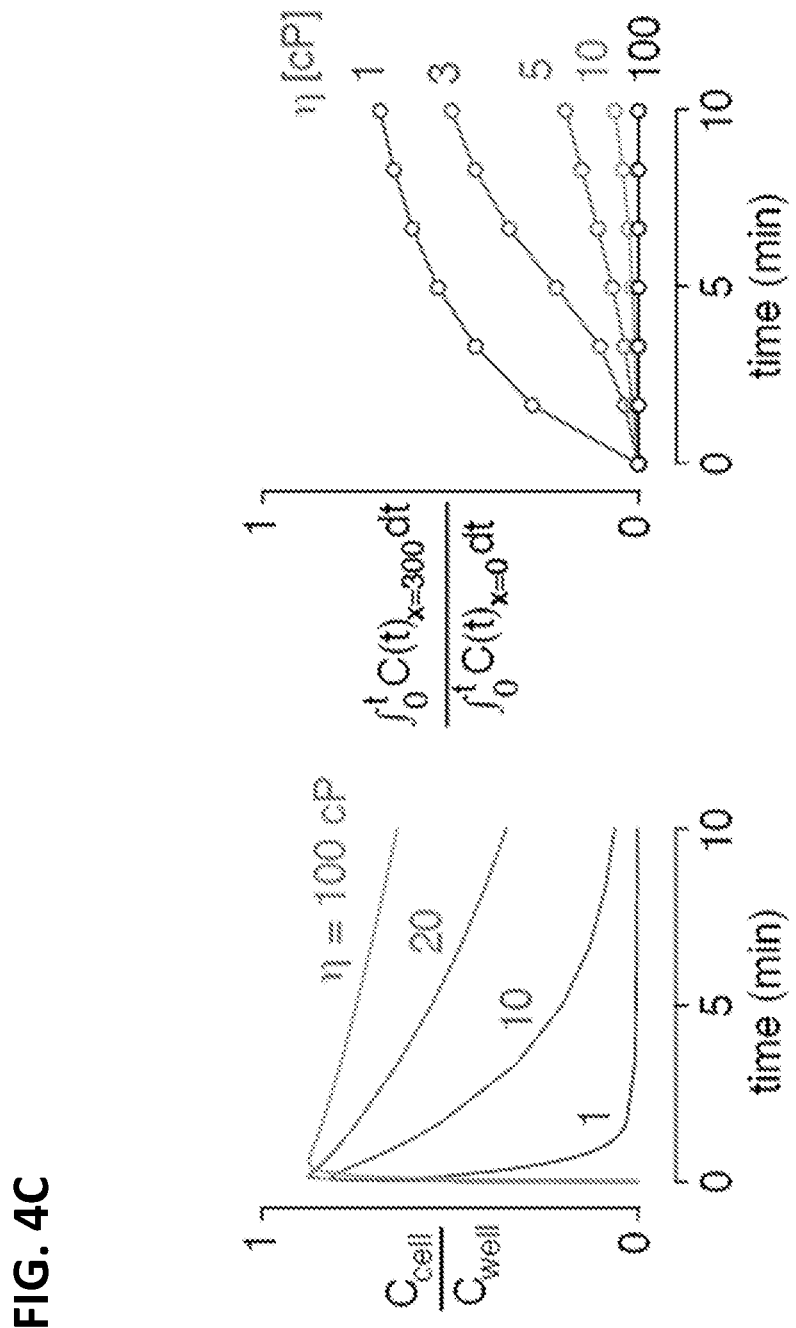

The hollow micropillar design was characterized using finite-element diffusion simulations. FIG. 4A depicts a modeled 5×5 hollow micropillar array with indicated geometry. Compound exposure to cells and cross-talk between neighboring compounds were analyzed for different solution viscosities and micropillar heights. FIG. 4B (left) depicts pseudocolor images of compound concentration with overlying solutions of relative viscosities 1 and 100 cP. As an initial condition, compound was uniformly distributed throughout the cylindrical volume of the central hollow micropillar, with zero concentration elsewhere. Rapid compound diffusion was found for $\eta=1$ cP, with compound seen in neighboring spots by 5 min; however, compound was not seen in the neighboring spots for $\eta=100$ cP. These observations were confirmed in concentration line scans in FIG. 4B (right). FIG. 4C (left) depicts relative compound concentration at the cell surface in the circular region of the central micropillar normalized to the original compound concentration in the micropillar well. Compound concentration at the cell surface remained high for at least 10 min for $\eta=100$ cP, and for lesser times with lower $\eta$.

Figure 8:
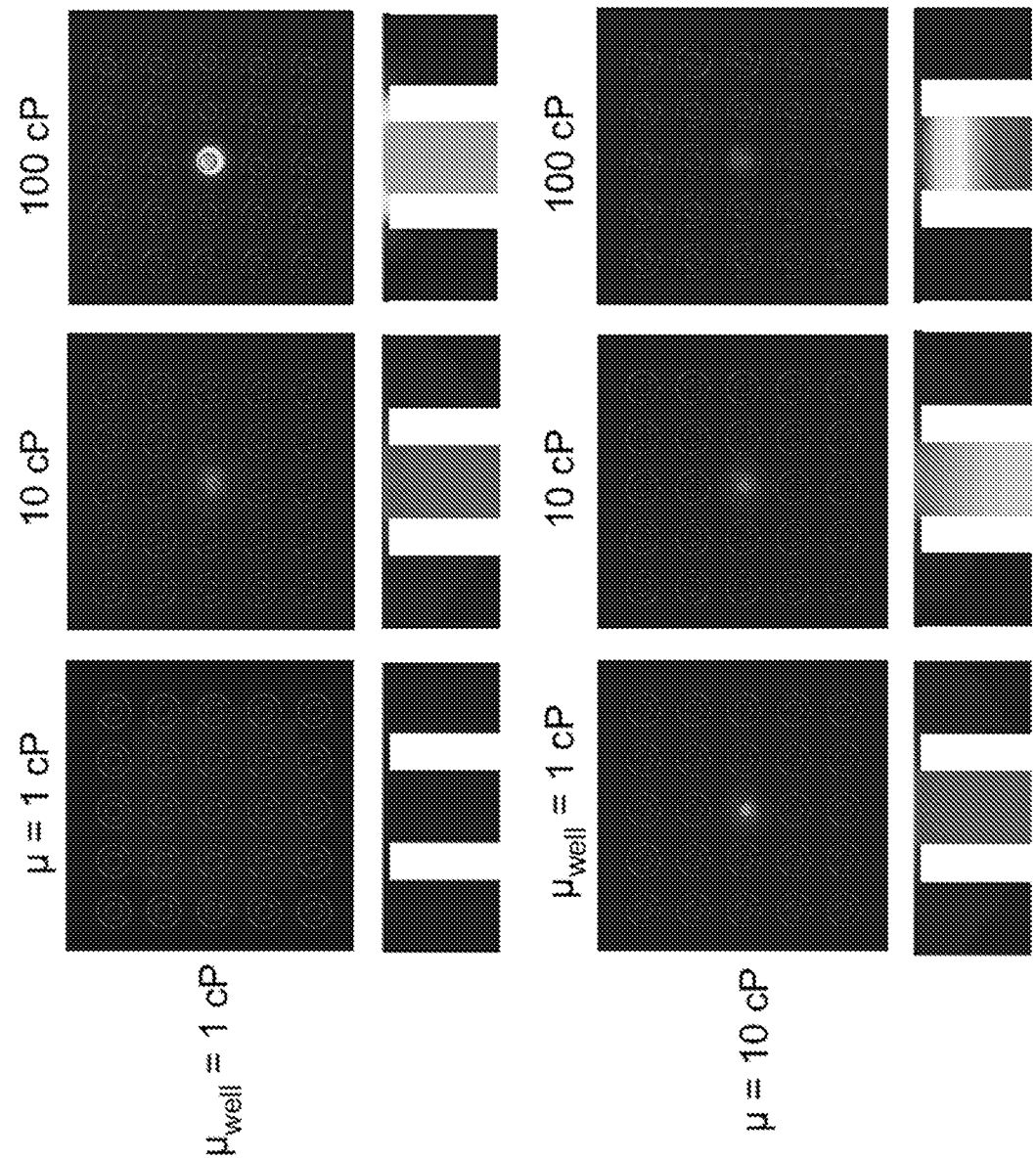
FIG. 8 depicts a computational modeling of compound release from hollow micropillars for different combinations of microwell solution viscosity $\mu_{well}$ and outside solution viscosity $\mu$.

Compound exposure was reduced, as expected, with increasing gap distance between the cell surface and the hollow micropillar (FIG. 5, right). Additional computational modeling (FIG. 7 and FIG. 8) of compound release from hollow micropillars was done for various combinations of microwell and outside solution viscosities, showing the expected slowed compound release with increased viscosity of the outside solution or of the alginate-containing well. Microwell solution viscosity $\mu_{well}$ was 1 cP, and outside solution viscosity $\mu$ was 1, 10 or 100 cP. Results were shown as pseudocolored 2-dimensional images at indicated times t (FIG. 7) and at t=300 s (FIG. 8).

Cross-talk was analyzed by computing compound concentration at the cell surface in the region of the central microfiber and at a neighboring spot. The time-integrated concentration at the neighboring spot ($\int C$ dt at x=300 μm) was normalized to that of the central spot ($\int C$ dt at x=0 μm). FIG. 4C (right) depicts a time course of compound exposure for indicated $\eta$ of overlying solution, where little or no cross-talk in 10 min for $\eta=10$ or 100 cP. Cross-talk from neighboring wells was quantified as time-integrated compound exposure in neighboring well normalized to that in central well. Additional computations investigated micropillar height and gap distance between the micropillars and the cell surface reduced micropillar height, reduced compound exposure (because of reduced compound amount), and increased cross-talk (because of reduced volume between micropillars). Compound exposure and cross-talk were relatively insensitive to a 2-fold change in gap distance. The fabricated hollow micropillar array was designed with about a 10 μm gap distance between the upper surface of micropillars and the cell layer. Computational and experimental demonstration of compound exposure to the cell layer in the vicinity of each hollow micropillar for more than 10 min resulted in less than 2% cross-talk for neighboring micropillar wells.

Example 3: Compound Formulation and Microdispensing

Compounds were dispensed in the hollow micropillar wells in a 1 nL volume total using microdispensing technology as described above. Following testing of different hydrogel materials, an alginate hydrogel was suitable using the methods disclosed herein. The alginate hydrogel (solidified upon contact with calcium chloride pre-coating micropillars) was found to effectively maintain compounds within hollow micropillars and allow their release into the overlying solution to diffuse and contact the cell layer. Alginate solutions remain liquid prior to contacting $CaCl_2$. Coating of the PDMS surface with polyethylene glycol (PEG) prevented compound adsorption to the PDMS. While convenient in manufacturing, PDMS can absorb small molecules such as drugs, and the hydrophobic PDMS surface can entrap air bubbles, which the design described herein could impair fluid contact between the micropillars and cell layer. A PEG-200 coating was used, which prevented compound absorption and air bubbles. PEG has been shown to produce stable, long-term PDMS surface modification.

For microdispensing, $CaCl_2$ was first dispensed, dried, and then compounds in a 1% alginate solution were dispensed. Testing of different compound solubilizing agents (for example, dimethylsulfoxide, DMSO; dimethylacetone, DMA) showed that DMSO up to 30% vol/vol did not interfere with alginate gelation and that compounds remained solubilized down to 5% vol/vol DMSO. Confocal microscopy using rhodamine 101 as test compound indicated that microdispensing produced uniform fluorescence throughout microwells, with fluorescence seen up to the top of each microwell. After microdispensing, storage of micropillar arrays in a humidified chamber prevented significant evaporation for at least several days.

Figure 6:
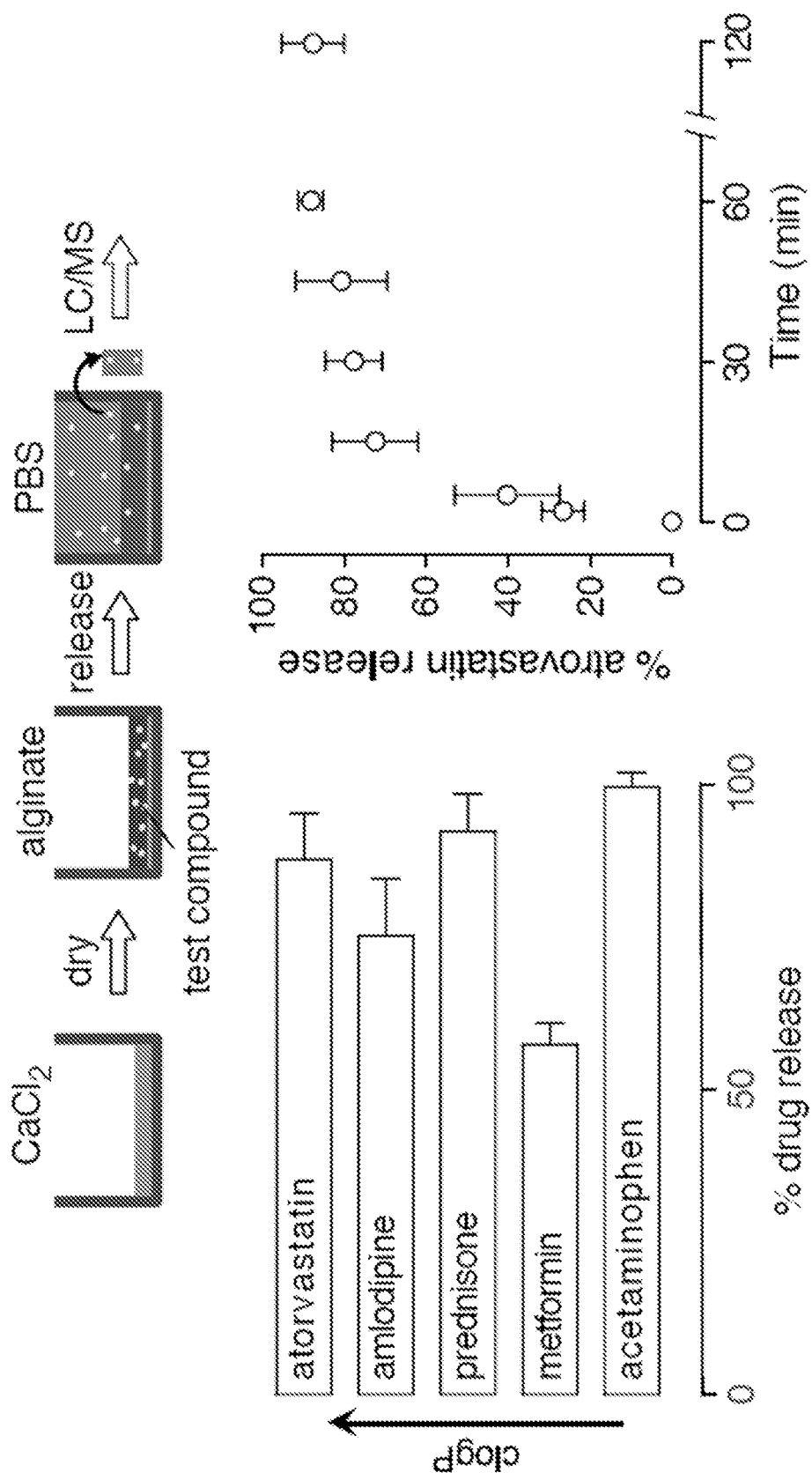
FIG. 6 depicts drug release from an alginate hydrogel using the methods and systems disclosed herein.
Figure 7:
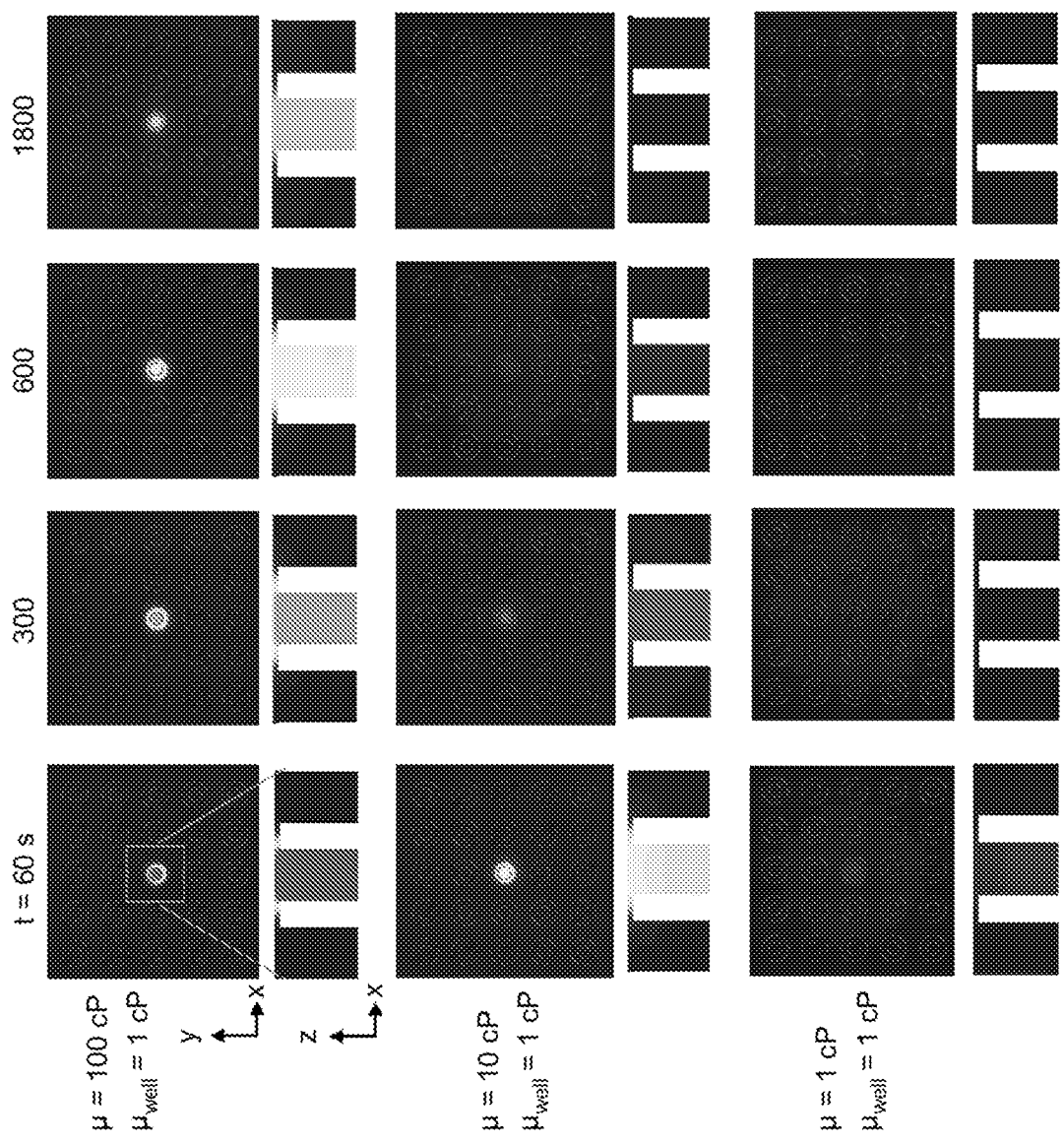
FIG. 7 depicts a computational modeling of compound release from hollow micropillars for different viscosity combinations.

To test the efficiency of compound release from alginate hydrogels, the release was tested of five commonly prescribed drugs with a wide range of c log P values from 0.91 (acetaminophen) to 5.3 (atorvastatin). Indicated drugs at 10 μm were dissolved in alginate hydrogels as disclosed herein, and after gelation, the hydrogel was covered with PBS at time zero as shown in FIG. 6 (top). Drug release into an overlying PBS solution was quantified by LC/MS at 3 hours (mean±S.E.M., n=3) as shown in FIG. 6 (left). FIG. 6 (left) depicts near complete release of four out of the five randomly chosen drugs tested, indicating reversible drug dissolution in the alginate hydrogel with minimal absorption into the PDMS substrate. More than 90% compound release from the alginate hydrogel was determined by LC/MS for a range of approved drugs with widely varying c log P. For one of the drugs (atorvastatin), the kinetics of release was quantified by assaying sampled fluid at different times. FIG. 6 (right) depicts that atorvastatin release from the hydrogel occurred with a half-time of about 10 min (mean±S.E.M., n=3), which was consistent with the expected time for its diffusion out of the cylindrical micropillar well.

Example 4: Release and Diffusion of a Fluorescent Dye from Hollow Microfibers

Figure 9A:
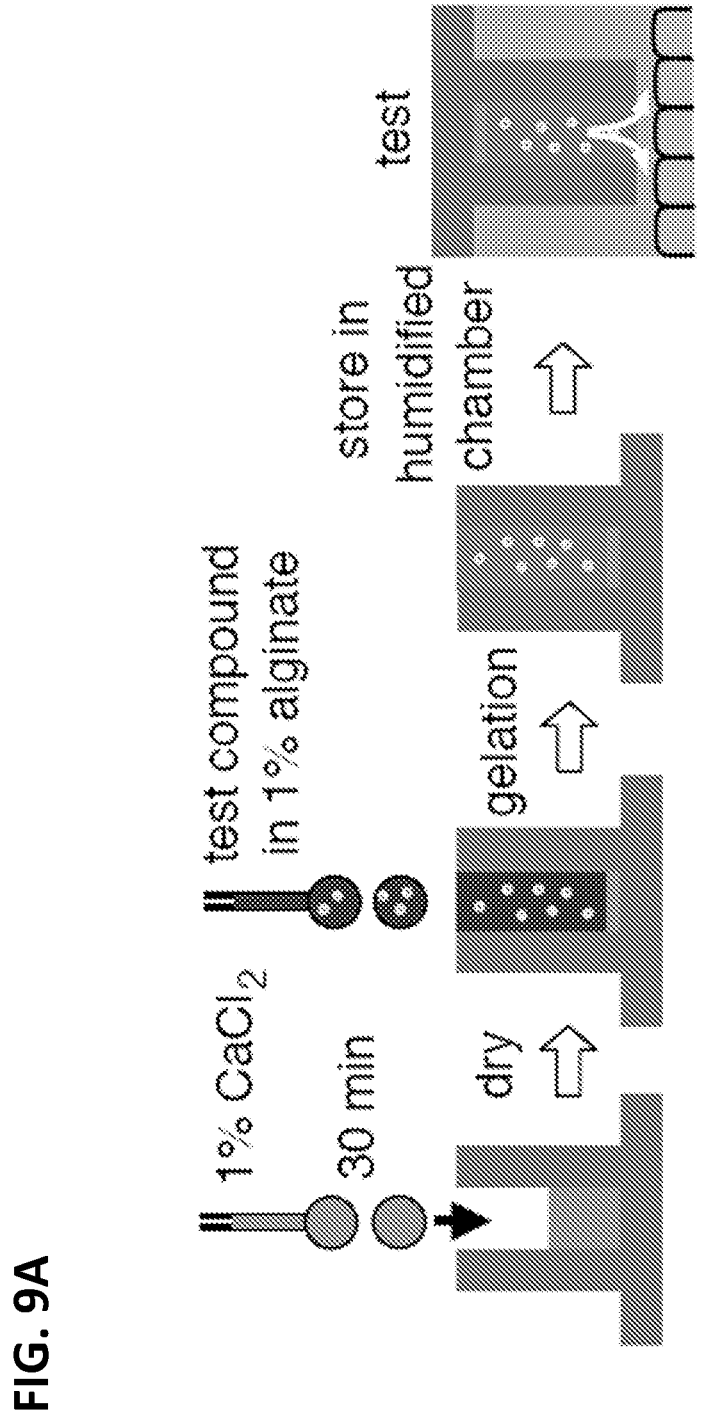
FIG. 9A-9C depict release and diffusion of fluorescent dye from hollow micropillars.
Figure 9B:
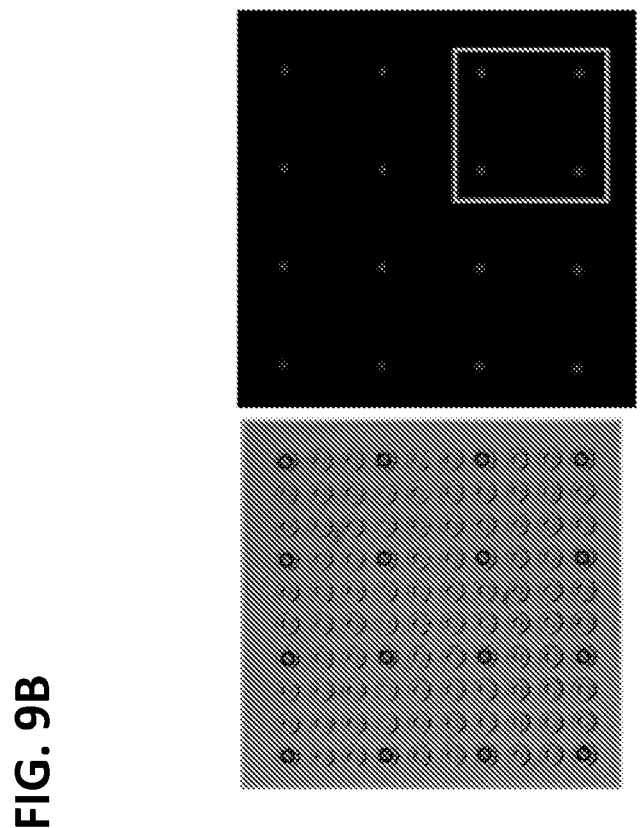
Figure 9C:
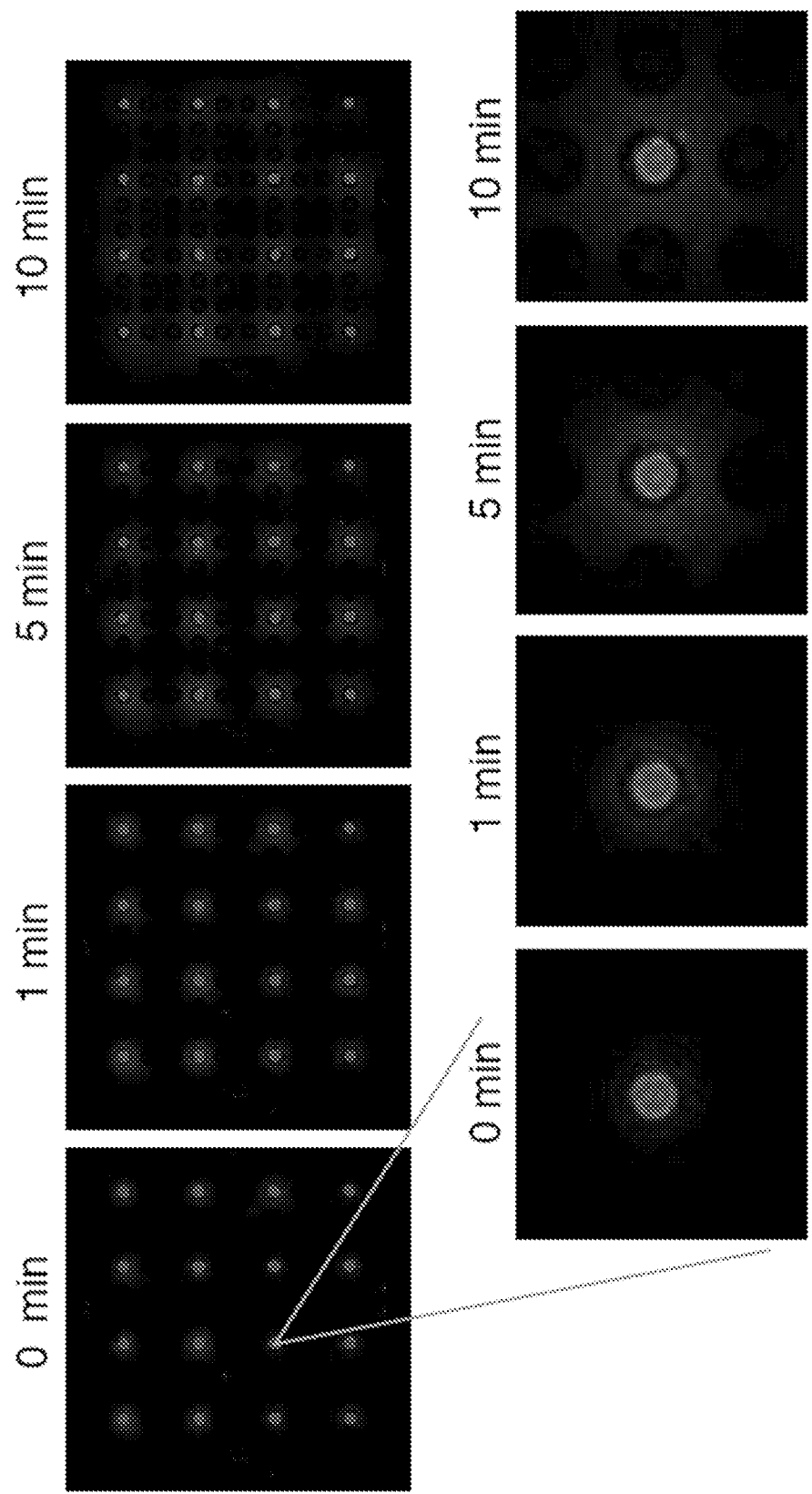

As experimental validation of the computational modeling, alginate was microdispensed into a 10×10 array of hollow microfibers with rhodamine 101 added to a subset of micropillars as shown in FIGS. 9A and 9B. For example, rhodamine 101 was added to a subset of micropillars as shown schematically in FIG. 9B (left) and by fluorescence microscopy in FIG. 9B (right). FIG. 9C depicts rhodamine 101 diffusion from the micropillar wells at indicated times after contacting a cell layer with a solution of relative viscosity 100 cP, as measured by confocal microscopy. Less than 2% of rhodamine 101 fluorescence was seen in neighboring wells at 10 min following addition of the 100 cP solution, confirming the absence of significant cross-talk.

Example 5: CFTR Activation Measurement on Filter-Grown Epithelial Cells

Figure 10:
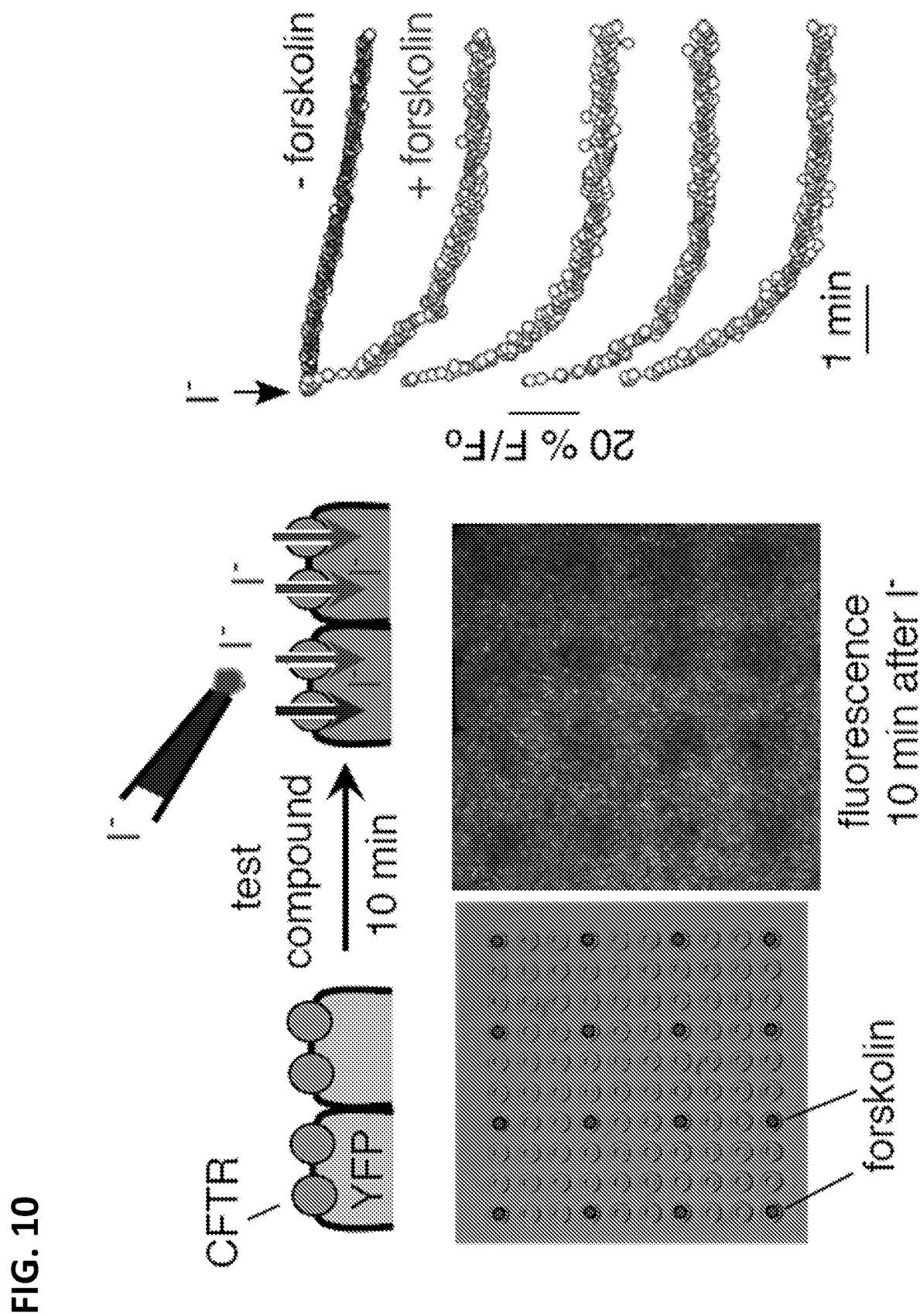
FIG. 10 depicts a CFTR activator assay using the methods and systems disclosed herein.

To demonstrate the utility of the hollow micropillar array design, CFTR activation was measured in FRT epithelial cells expressing human CFTR and a genetically encoded yellow fluorescent protein (YFP) cytoplasmic halide sensor. CFTR function was determined from the kinetics of YFP fluorescence quenching following addition of an iodide-containing solution on the apical surface of the cell monolayer. Proof of concept was determined using the 10×10 hollow micropillar array in epithelial cells expressing human CFTR and YFP, in which a CFTR activator (forskolin) was present in randomly selected micropillars. The cells were cultured on a porous transwell filter. As shown in FIG. 10 (top left), following extracellular iodide ($I^-$) addition, CFTR activation by the cAMP agonist forskolin allowed $I^-$ entry into cells and consequent quenching of cytoplasmic YFP fluorescence.

A 10×10 hollow micropillar array, as used in validation studies described herein, was loaded with alginate hydrogels, some of which contained 10 μM forskolin as shown in FIG. 10 (bottom left). After contacting the cell layer for 10 min, the overlying solution was exchanged to an $I^-$-containing solution. A YFP fluorescence image taken at 10 min as showed reduced fluorescence in cells overlying (and nearby) forskolin-loaded micropillars. FIG. 10 (right) depicts deduced kinetics of fluorescence quenching following $I^-$ addition in which the fluorescence signal was integrated over 100 μm circles in cells overlying forskolin-containing micropillars ("+forskolin"; four examples shown) and a neighboring area of cells ("−forskolin"). Forskolin activation of CFTR increased initial curve slope by more than 14-fold, with full-field analysis giving a robust assay statistical Z-factor >0.65, indicating the ability to identify activators with a high level of confidence.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. Mayr, L. M.; Bojanic, D. Novel trends in high-throughput screening. *Curr. Opin. Pharmacol.* 2009, 9, 580-588.
2. Cheong, R.; Paliwal, S.; Levchenko, A. High-content screening in microfluidic devices. *Expert Opin. Drug Discov.* 2010, 5, 715-720.
3. Bellomo, F. Medina, D. L.; De Leo, E.; Panarella, A.; Emma, F. High-content drug screening for rare diseases. *J. Inherit. Metab. Dis.* 2017, 40, 601-607.
4. Nickischer, D.; Elkin, L.; Cloutier, N.; O'Connell, J.; Banks, M.; Weston, A. Challenges and opportunities in enabling high-throughput, miniaturized high content screening. *Methods Mol. Biol.* 2018, 1683, 165-191.
5. Hanrahan, J. W.; Matthes, E.; Carlile, G.; Thomas, D. Y. Corrector combination therapies for F508del-CFTR. *Curr. Opin. Pharmacol.* 2017, 34, 105-111.
6. Mijnders, M.; Kleizen, B.; Braakman, I. Correcting CFTR folding defects by small molecule correctors to cure cystic fibrosis. *Curr. Opin. Pharmacol.* 2017, 34, 83-90.
7. Li, H.; Pesce, E.; Sheppard, D. N.; Singh, A. K.; Pedemonte, N. Therapeutic approaches to CFTR dysfunction: From discovery to drug development. *J. Cyst. Fibros.* 2017, DOI:10.1016/j.jcf.2017.08.013.

8. Edemonte, N.; Tomati, V.; Sondo, E.; Galietta. L. J. Influence of cell background on pharmacological rescue of mutant CFTR. *Am. J. Physiol. Cell Physiol.* 2010, 298, C866-874.
9. Kwon, C. H.; Wheeldon, I.; Kachouie, N. N.; Lee, S. H.; Bae, H.; Sant, S.; Fukuda, J.; Kang, J. W.; Khademhosseini, A. Drug-eluting microarrays for cell-based screening of chemical-induced apoptosis. *Anal. Chem.*, 2011, 83, 4118-4125.
10. Lee, D. W.; Choi, Y.-S.; Seo, Y. J.; Lee, M.-Y.; Jeon, S. Y.; Ku, B.; Kim, S.; Yi, S. H.; Nam, D.-H. High-throughput screening (HTS) of anticancer drug efficacy on a micropillar/microwell chip platform. *Anal. Chem.*, 2014, 86, 535-542.
11. Ding, Y.; Li, J.; Xiao, W.; Xiao, K.; Lee, J.; Bhardwaj, U.; Zhu, Z.; Digiglio, P.; Yang, G.; Lam, K. S.; Pan, T. Microfluidic-enabled print-to-screen platform for high-throughput screening of combinatorial chemotherapy. *Anal. Chem.*, 2015, 87, 10166-10171.
12. Fujita, S.; Onuki-Nagasaki, R.; Ikota, K.; Hara, Y. A simple method for producing multiple copies of controlled release small molecule microarrays for cell-based screening, *Biofabrication,* 2016, 9, 011001.
13. Bailey, S. N.; Sabatini, D. M.; Stockwell, B. R. Microarrays of small molecules embedded in biodegradable polymers for use in mammalian cell-based screens, *Proc. Natl. Acad. Sci. USA.* 2004, 101, 46, 16144-16149.
14. Jin, B. J.; Ko, E. A.; Namkung, W.; Verkman, A. S. Microfluidics platform for single-shot dose response analysis of chloride channel modulating compounds. *Lab Chip* 2013, 13, 3862-3867.
15. Cil, O.; Phuan, P. W.; Lee, S.; Tan, J.; Haggie, P. M.; Levin, M. H.; Sun, L.; Thiagarajah, J. R.; Ma, T.; Verkman, A. S. CFTR activator increases intestinal fluid secretion and normalizes stool output in a mouse model of constipation. *Cell. Mol. Gastroentrol. Hepatol.* 2016, 2, 317-327.
16. Whitesides, G. M.; Ostuni, E.; Takayama, S.; Jiang, X.; Ingber, D. E. Soft lithography in biology and biochemistry Annu. Rev. *Biomed. Eng.* 2001, 3, 335-373.
17. Van Meer, B. J.; De Vries, H.; Firth, K. S. A.; Van Weerd, J.; Tertoolen, L. J. G.; Karperien, H. B. J.; Jonkheijm, P.; Denning, C.; IJzerman, A. P.; Mummerya, C. L. Small molecule absorption by PDMS in the context of drug response bioassays. *Biochem. Biophys. Res. Commun.* 2017, 482, 323-328.
18. Hellmich, W.; Regtmeier, J.; Duong, T. T.; Ros, R.; Anselmetti, D.; Ros, A. Poly(oxyethylene) based surface coatings for poly(dimethylsiloxane) microchannels, *Langmuir,* 2005, 21, 7551-7557.
19. Huang, B.; Wu, H.; Kim, S.; Zare, R. N. Coating of poly(dimethylsiloxane) with n-dodecyl-β-Dmaltoside to minimize nonspecific protein adsorption, *Lab Chip,* 2005, 5, 1005-1007.
20. Wang, J. D.; Douville, N. J.; Takayama, S.; Elsayed, M. Quantitative analysis of molecular absorption into PDMS microfluidic channels, *Ann Biomed Eng.* 2012, 40, 1862-1873.
21. Lillehoj, P. B.; Wei, F.; Ho, C.-M. A self-pumping lab-on-a-chip for rapid detection of botulinum toxin, *Lab Chip,* 2010, 10, 2265-2270.
22. Lillehoj, P. B.; Ho, C.-M. A long-term, stable hydrophilic poly(dimethylsiloxane) coating for capillary based pumping. *Proceedings of the IEEE 23rd International Conference on Micro Electro Mechanical Systems (MEMS)* 2010, 1063-1066. DOI: 10.1109/MEMSYS.2010.5442393
23. Demming, S.; Lesche, C.; Schmolke, H.; Klages, C.-P.; Buttgenbach, S. Characterization of long-term stability of hydrophilized PEG-grafted PDMS within different media for biotechnological and pharmaceutical applications. *Phys. Status Solid. A* 2011, 288, 1301-1307.
24. Alvarez-Lorenzo, C.; Blanco-Fernandez, B.; Puga, A. M.; Concheiro, A. Crosslinked ionic polysaccharides for stimuli-sensitive drug delivery. *Adv. Drug Deliv. Rev.* 2013, 65, 1148-1171.
25. Tanaka, H.; Matsumura, M.; Veliky, I. A. Diffusion characteristics of substrates in Ca-Alginate gel beads, *Biotechnol. Bioeng.* 1984, 26, 53-58.
26. Mazutis, L.; Vasiliauskas, R.; Weitz, D. A. Microfluidic production of alginate hydrogel particles for antibody encapsulation and release. *Macromol. Biosci.* 2015, 15, 1641-1646.
27. Lee, K. Y.; Mooney, D. J. Alginate: properties and biomedical applications. *Prog Polym Sci.* 2012, 37, 106-126.
28. Jin, B. J., C. Esteva-Font and A. S. Verkman (2015). Droplet-based microfluidic platform for measurement of rapid erythrocyte water transport. *Lab Chip* 15:3380-3390.
29. Jin, B. J. and A. S. Verkman (2017). Microfluidic platform for rapid measurement of transepithelial water transport. *Lab Chip* 17:887-895.
30. Verkman, A. S. and L. J. Galietta (2009). Chloride channels as drug targets. *Nature Reviews Drug Discovery* 8:153-171.
31. Verkman, A. S., M. O. Anderson and M. C. Papadopoulos (2014). Aquaporins: important but elusive drug targets. *Nature Reviews Drug Discovery* 13:259-277.
32. Papadopoulos, M. C., J. L. Bennett and A. S. Verkman (2014). Treatment of neuromyelitis optica: state-of-the-art and emerging therapies. *Nature Reviews Neurology* 10:493-506.
33. Esteva-Font, C., M. O. Anderson and A. S. Verkman (2015). Urea transporter proteins as targets for small-molecule diuretics. *Nature Reviews Nephrology* 11:113-123.
34. Thiajarajah, J. R., M. Donowitz and A. S. Verkman (2015). Secretory diarrhea: mechanisms and emerging therapies. *Nature Reviews Gastroenterology Hepatology* 12:446-457.

What is claimed is:

1. A method of screening a candidate agent to determine whether the candidate agent modulates an activity of cultured cells, the method comprising:
   positioning a hydrogel comprising at least one candidate agent in a lumen of a hollow micropillar, wherein the hollow micropillar comprises a first surface having an open end and a second surface having a closed end in contact with a first substrate, wherein the hollow micropillar is orthogonal to the first substrate;
   bringing the first surface of the hollow micropillar into communication with a surface of cultured cells on a second substrate to provide an interaction gap between the first surface of the hollow micropillar and the surface of the cultured cells, wherein the first surface of the hollow micropillar is in a spaced apart and in facing relationship with the surface of cultured cells;
   adding a solution to the interaction gap such that the at least one candidate agent is released from the hydrogel onto the surface of cultured cells; and
   measuring a signal from the cultured cells, wherein the signal indicates whether the at least one candidate agent modulates the activity of the cultured cells.

2. The method of claim 1, wherein the hydrogel comprises alginate.

3. The method of claim 1, wherein the at least one candidate agent comprises at least two candidate agents.

4. The method of claim 1, wherein the at least one candidate agent comprises at least one thousand candidate agents.

5. The method of claim 1, wherein the positioning comprises filling the lumen of the hollow micropillar such that a surface of the hydrogel in the lumen is coplanar with the first surface of the hollow micropillar.

6. The method of claim 1, wherein the positioning comprises filling a portion of the lumen of the hollow micropillar.

7. The method of claim 1, wherein the positioning comprises printing the hydrogel by microinjection in the lumen of the hollow micropillar.

8. The method of claim 1, wherein the hollow micropillar comprises an inner diameter and an outer diameter.

9. The method of claim 8, wherein the inner diameter is 50-600 microns.

10. The method of claim 8, wherein the outer diameter is 60-900 microns.

11. The method of claim 1, wherein the hollow micropillar comprises a coating layer.

12. The method of claim 11, wherein the coating layer is hydrophilic.

13. The method of claim 1, wherein the hollow micropillar has a height of 50-600 microns.

14. The method of claim 1, wherein the first substrate comprises polydimethylsiloxane.

15. The method of claim 1, wherein the cultured cells comprise non-epithelial cells.

16. The method of claim 1, wherein the cultured cells comprise epithelial cells.

17. The method of claim 16, wherein the cultured cells comprise filter-grown epithelial cells.

18. The method of claim 16, wherein the epithelial cells express the cystic fibrosis transmembrane conductance regulator chloride (CFTR) channel.

19. The method of claim 1, wherein the first surface of the hollow micropillar is in a spaced apart and in facing relationship with an apical surface of the cultured cells.

20. The method of claim 1, wherein the second substrate comprises polydimethylsiloxane.

21. The method of claim 1, wherein the interaction gap has a width of 10 microns.

22. The method of claim 1, wherein the interaction gap has a width of 5 microns.

23. The method of claim 1, wherein the first substrate is held parallel to the second substrate.

24. The method of claim 23, wherein the first substrate of the hollow micropillar is held parallel to the second substrate by a force.

25. The method of claim 24, wherein the force is a magnetic force.

26. The method of claim 24, wherein the force is an electrical force.

27. The method of claim 1, wherein the first substrate of the hollow micropillar is held parallel to the second substrate by a support device.

28. The method of claim 27, wherein the support device is a clamp.

29. The method of claim 27, wherein the support device is a spacer and wherein the spacer is positioned between the first substrate of the hollow micropillar and the second substrate.

30. The method of claim 29, wherein the spacer has a height greater than the height of the hollow micropillar.

31. The method of claim 29, wherein the spacer comprises a rectangular shape.

32. The method of claim 1, wherein the adding comprises adding a buffer solution to the interaction gap.

33. The method of claim 32, wherein the buffer solution comprises phosphate-buffered saline.

34. The method of claim 32, wherein the buffer solution comprises chloride.

35. The method of claim 32, wherein the buffer solution comprises iodide.

36. The method of claim 32, wherein the buffer solution is manually added.

37. The method of claim 1, the method further comprising determining an amount of the at least one candidate agent released from the hydrogel onto the surface of cultured cells.

38. The method of claim 37, wherein the determining comprises performing mass spectrometry.

39. The method of claim 1, wherein the measuring comprises measuring an optical signal.

40. The method of claim 1, wherein the measuring comprises measuring a fluorescent signal.

41. The method of claim 1, wherein the first substrate is in contact with a plurality of hollow micropillars.

42. The method of claim 41, wherein the plurality of hollow micropillars comprises two or more hollow micropillars.

43. The method of claim 41, wherein the plurality of hollow micropillars comprises three or more hollow micropillars.

44. The method of claim 41, wherein the hydrogel comprising the at least one candidate agent is positioned in the lumen of each hollow micropillar of the plurality of hollow micropillars.

45. The method of claim 41, wherein each hollow micropillar is positioned at a set distance apart such that crosstalk between each hollow micropillar is reduced.

46. The method of claim 45, wherein crosstalk between each hollow micropillar is less than 2%.

47. The method of claim 45, wherein the set distance is the same between each hollow micropillar.

48. The method of claim 45, wherein the set distance is 100-1000 microns.

49. The method of claim 1, the method further comprising increasing viscosity of the solution added to the interaction gap such that crosstalk is reduced.

50. The method of claim 49, wherein the increasing viscosity comprises adding methylcellulose to the solution.

* * * * *

UNITED STATES PATENT AND TRADEMARK OFFICE
CERTIFICATE OF CORRECTION

PATENT NO. : 12,038,430 B2  
APPLICATION NO. : 17/046099  
DATED : July 16, 2024  
INVENTOR(S) : Alan S. Verkman et al.

Page 1 of 1

It is certified that error appears in the above-identified patent and that said Letters Patent is hereby corrected as shown below:

In the Claims

In Column 3, Line 49, delete "micropillar" and insert -- micropillar. --.

In Column 7, Line 61, delete "c log P" and insert -- clogP --.

In Column 7, Line 67, delete "(1→4)β-" and insert -- (1→4)-β- --.

In Column 28, Line 47, delete "Germany)" and insert -- Germany). --.

In Column 29, Line 11, delete "C)" and insert -- $C_{well}$), --.

In Column 33, Line 26, delete "c log P" and insert -- clogP --.

In Column 33, Line 38, delete "c log P." and insert -- clogP. --.

In Column 35, Line 20, delete "Ikota," and insert -- Ikuta, --.

In Column 35, Line 36, delete "Gastroentrol." and insert -- Gastroenterol. --.

Signed and Sealed this  
Twenty-sixth Day of November, 2024

Katherine Kelly Vidal  
*Director of the United States Patent and Trademark Office*